(12) United States Patent
Baaske et al.

(10) Patent No.: US 10,488,326 B2
(45) Date of Patent: Nov. 26, 2019

(54) CAPILLARY ARRAY

(71) Applicants: Philipp Baaske, Munich (DE); Stefan Duhr, Munich (DE); Stefan Reichl, Munich (DE); Hans-Jurgen Bigus, Pliezhausen (DE)

(72) Inventors: Philipp Baaske, Munich (DE); Stefan Duhr, Munich (DE); Stefan Reichl, Munich (DE); Hans-Jurgen Bigus, Pliezhausen (DE)

(73) Assignee: NANOTEMPER TECHNOLOGIES GMBH, Munich (DE)

( * ) Notice: Subject to any disclaimer, the term of this patent is extended or adjusted under 35 U.S.C. 154(b) by 0 days.

(21) Appl. No.: 14/484,640

(22) Filed: Sep. 12, 2014

(65) Prior Publication Data
US 2015/0137005 A1 May 21, 2015

(30) Foreign Application Priority Data
Sep. 13, 2013 (EP) .................................... 13184379

(51) Int. Cl.
| | |
|---|---|
| G01N 21/03 | (2006.01) |
| B01L 9/06 | (2006.01) |
| G01N 21/11 | (2006.01) |
| G01N 21/13 | (2006.01) |
| G01N 21/71 | (2006.01) |
| B01L 7/00 | (2006.01) |

(52) U.S. Cl.
CPC .............. *G01N 21/03* (2013.01); *B01L 9/065* (2013.01); *G01N 21/11* (2013.01); *G01N 21/13* (2013.01); *G01N 21/71* (2013.01); *B01L 7/00* (2013.01); *B01L 2300/0838* (2013.01); *B01L 2400/0406* (2013.01); *G01N 2201/02* (2013.01); *G01N 2201/04* (2013.01)

(58) Field of Classification Search
CPC ....................................................... B01L 9/065
See application file for complete search history.

(56) References Cited

U.S. PATENT DOCUMENTS

| | | | | |
|---|---|---|---|---|
| 4,090,920 A | * | 5/1978 | Studer, Jr. ............ | C12M 41/36 435/288.4 |
| 2003/0165409 A1 | | 9/2003 | Macomber | |

(Continued)

FOREIGN PATENT DOCUMENTS

| | | |
|---|---|---|
| DE | 10 2011 054 998 A1 | 5/2013 |
| EP | 1 695 762 A | 8/2006 |

(Continued)

OTHER PUBLICATIONS

Office Action for German Patent Application No. 14 184 674.1-1371, dated Aug. 23, 2016, 6 pages.

(Continued)

*Primary Examiner* — Matthew D Krcha
(74) *Attorney, Agent, or Firm* — Westman, Champlin & Koehler, P.A.

(57) ABSTRACT

The invention relates to arrays with a plurality of capillaries being arranged in a plane and mechanically attached to the array, wherein the distance of adjacent capillaries is approximately 2.25 mm or an integer multiple thereof. At least one free end of each capillary projects from the array in such a way that the free ends of the capillaries may be simultaneously inserted into wells of a microwell plate.

18 Claims, 13 Drawing Sheets

(56) References Cited

U.S. PATENT DOCUMENTS

| | | | |
|---|---|---|---|
| 2005/0186122 A1* | 8/2005 | Mercer | B01L 9/52 422/400 |
| 2006/0131196 A1* | 6/2006 | Fuhr | A01N 1/02 206/438 |
| 2008/0099348 A1* | 5/2008 | Naylor | B65D 81/2076 206/0.6 |
| 2010/0136632 A1 | 6/2010 | Lipscomb et al. | |

FOREIGN PATENT DOCUMENTS

| | | | |
|---|---|---|---|
| EP | 2 572 787 A1 | 3/2013 | |
| WO | WO 0121310 A2 * | 3/2001 | B01D 61/18 |
| WO | WO 03066667 A2 * | 8/2003 | B01L 3/0241 |

OTHER PUBLICATIONS

Extended European Search Report for European Patent Application No. 14184674.1-1361, dated Jan. 12, 2015, 7 pages.

"Corning Life Sciences Microplate Dimensions for Corning 96 Well Microplates", 360 10.67 6.86 / 4.57 127, Mar. 13, 2009 (Mar. 13, 2009), Seiten 85-85, XP055328708; http://www.level.com/tw/html/ezatfiles/vipweb20/img/img/20297/MD_Microplate_Dimension_Sheets_96_Well.pdf.

Office Action for European Patent Application No. 13 184 379.9 1371, dated Dec. 20, 2016, 5 pages.

* cited by examiner

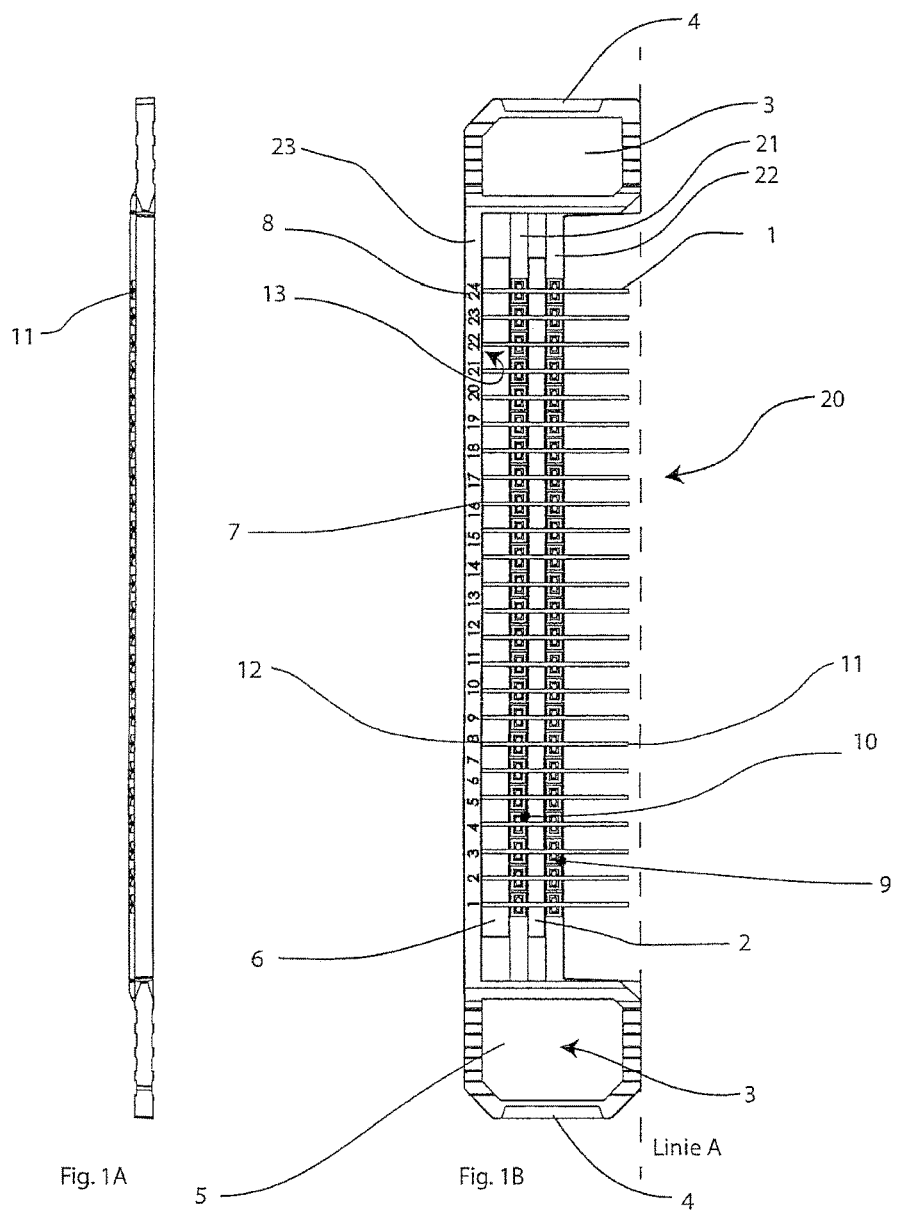
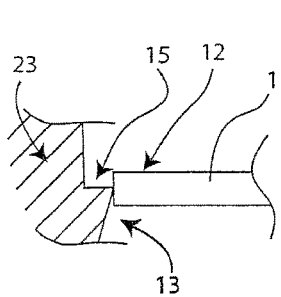
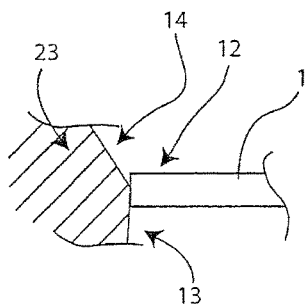
Fig. 1A   Fig. 1B   Fig. 1C   Fig. 1D

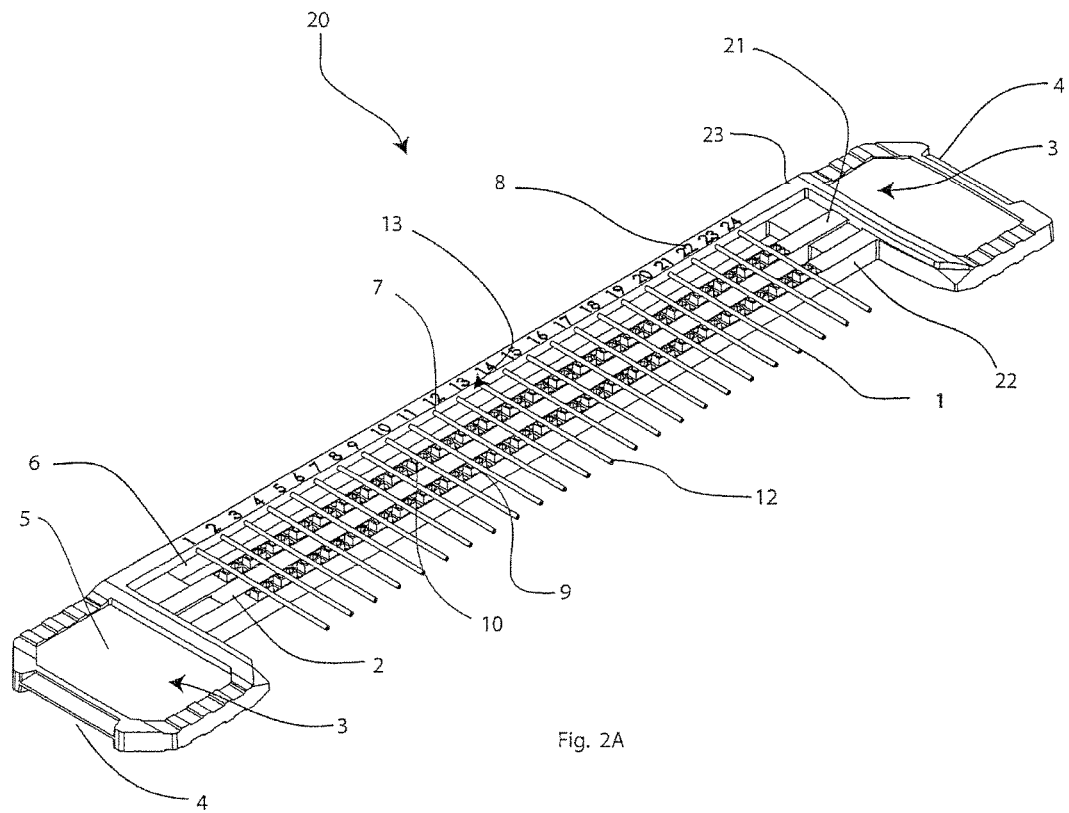
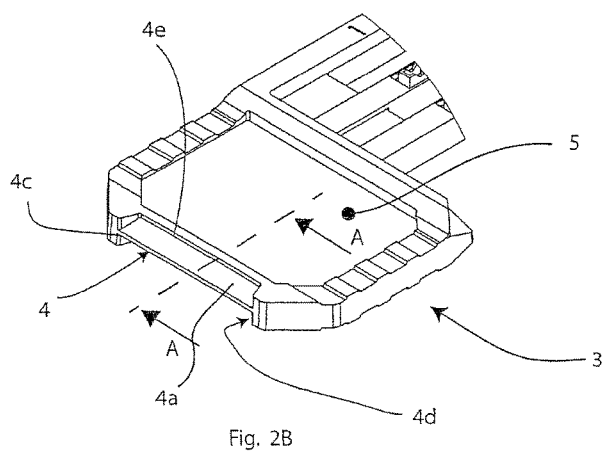
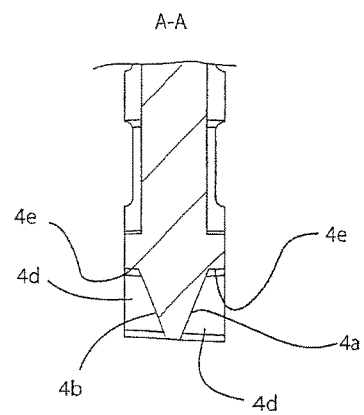
Fig. 2A
Fig. 2B
Fig. 2C

Fig. 5-1
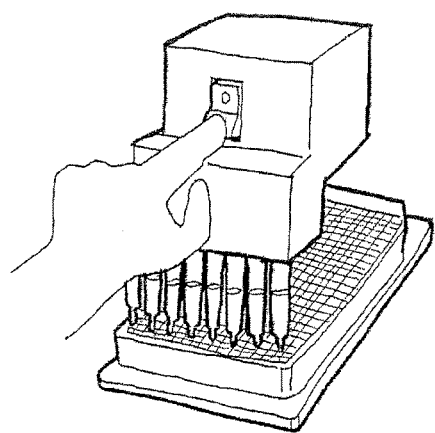
Fig. 5-2a
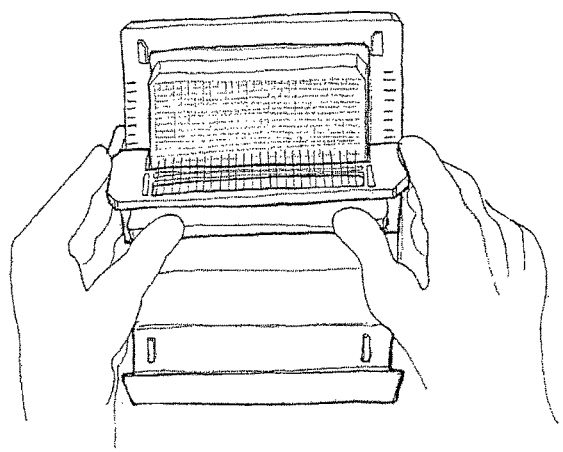
Fig. 5-3
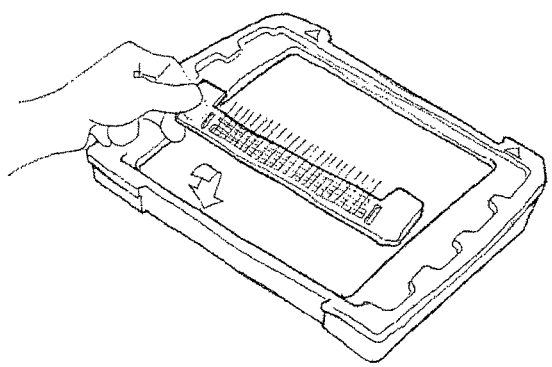
Fig. 5-2b
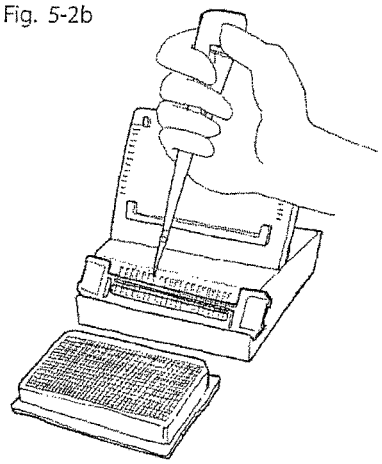
Fig. 5-4
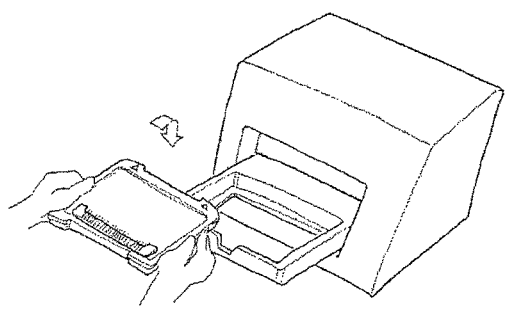
Fig. 5-5
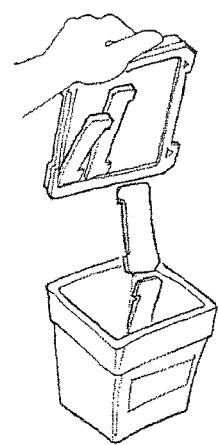
Fig. 5

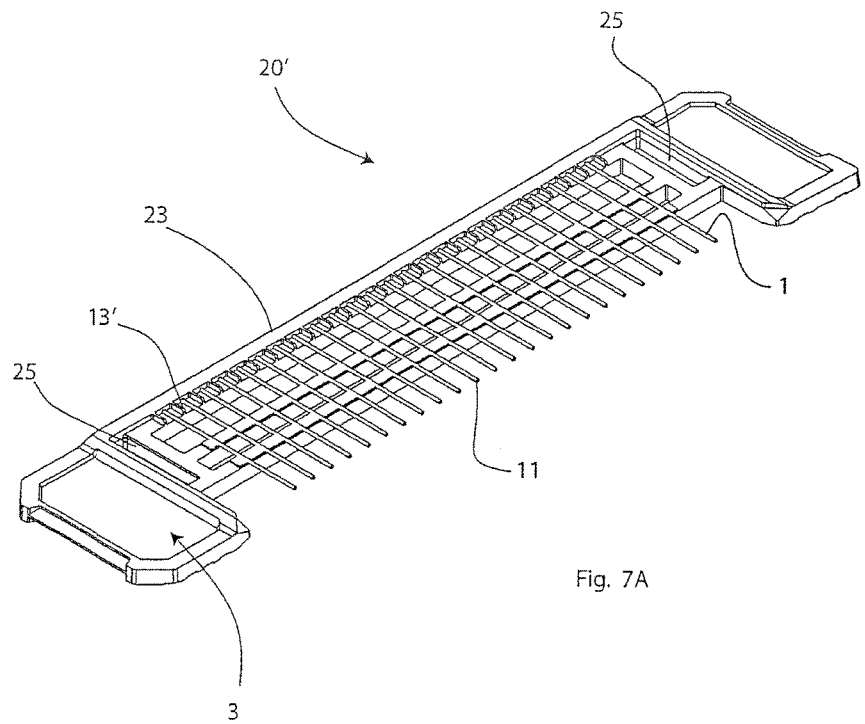
Fig. 7A
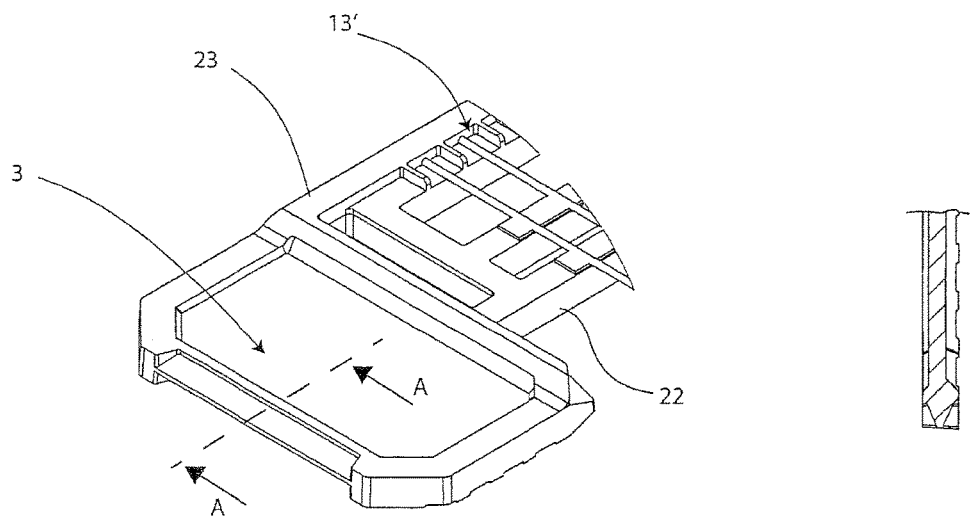
Fig. 7B
Fig. 7C

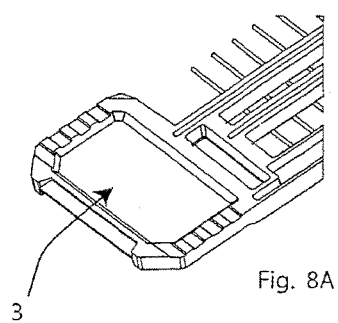
Fig. 8A
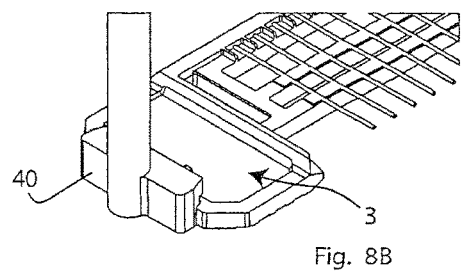
Fig. 8B
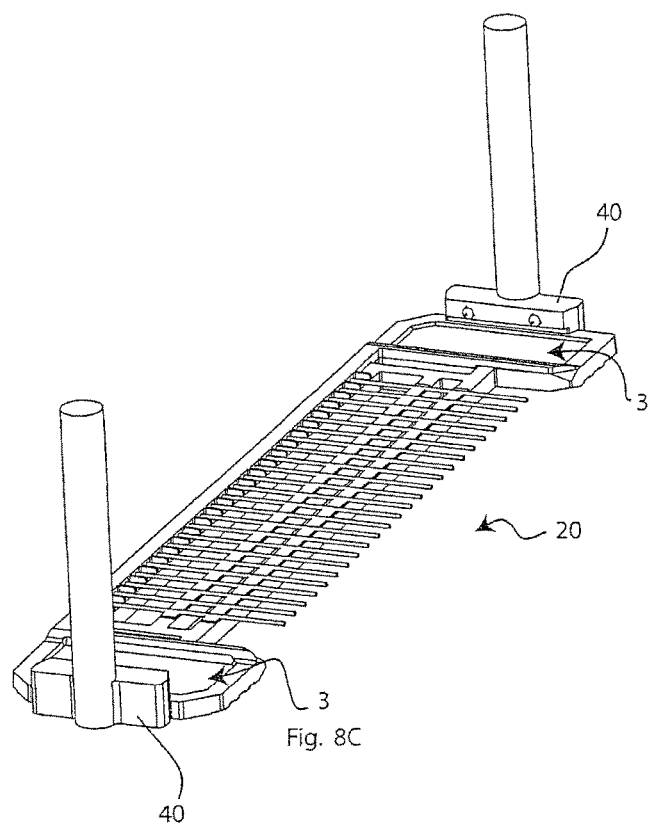
Fig. 8C
Fig. 8

SCHNITT A-A

CAPILLARY ARRAY

The present invention generally relates to a capillary array. In particular, the invention relates to an array for a plurality of capillaries by means of which a simultaneous filling of a plurality of capillaries of a microwell plate is made possible. Furthermore, the invention also relates to an apparatus and a method for filling, transportation and measurement of fluids having volumes at microlitre levels.

BACKGROUND OF THE INVENTION

NanoTemper Technologies GmbH develops and sells measurement devices, by means of which liquids within a capillary are examined or analyzed optically. It is further known that a single capillary is taken by hand, immersed into a liquid and then separately put down on an array and subsequently pushed into the measuring device. The individual filling is advantageous for certain single samples, however, if larger amounts of samples are to be examined, said method requires many steps which cannot readily be automated.

Application no. EP 2 572 787, which was filed by the same applicant as the present invention, describes capillaries which are adhered to an array by means of magnetic forces. Said method allows, i.a., easier and/or more precise positioning of the single capillaries on the array. In other words, it is still preferred to individually fill the single capillaries, however, the subsequent step is supported by magnetic forces.

However, in some biochemical/biological/diagnostic/medical appliances, magnetic beads in the liquids are used. Said substances or "magnetic beads" cannot be used with the magnetic capillaries since they are negatively influenced by the magnetic fields, for example by the magnetic fields holding the magnetic capillaries or by the magnetic material on the capillary itself.

Also in scopes of application like NMR (nuclear magnetic resonance), which also uses magnetic fields, magnetic capillaries cannot be applied.

A micro cuvette array, Optim 1000 of ForteBio is known, in which 16 micro cuvettes are arranged in recesses of an array and are filled separately or by means of a multichannel pipette. The array has to be sealed after filling the micro cuvettes and is then led to an analysis device. Filling of said micro cuvettes can, however, only be carried out manually in a cumbersome way. Furthermore, filling of said micro cuvettes cannot easily be followed or checked and the micro cuvettes are so short that vaporization of the liquid is a huge problem which makes elaborate sealing necessary.

For laboratory analyses microwell plates are often used. However, it is not possible to use said microwell plates for all laboratory analyses. For example, it is not possible for the time being to directly conduct thermophoresis measurements within the wells of said microwell plates.

Thus, there is the need for an improved device or an improved method. Preferably, it should be allowed to fill a plurality of capillaries simultaneously and preferably in a secure and efficient way as well as by simple and advantageous handling.

SUMMARY OF THE INVENTION

The device according to the present invention as well as the method according to the present invention is defined by the features of the independent claims. Advantageous embodiments are described in the subclaims.

The device according to the present invention, in the following also referred to as array, carrier, chip or support, is supposed to preferably hold a plurality of capillaries which are for example used for optical thermophoresis measurements or microscale thermophoresis measurements, preferably in the devices of NanoTemper Technologies GmbH. The plurality of capillaries are preferably arranged in a plane and mechanically attached to the array, wherein the distance between adjacent capillaries amounts to preferably 2.25 mm or an integer multiple thereof. At least one first free end of each capillary projects from the array in such a way that said free ends of the capillaries may be inserted simultaneously into the wells of a microwell plate.

The plane of the array in which the capillaries are arranged is referred to as x-y plane in the following. The height/thickness of the array extends perpendicular to said plane (z-direction). Upper and lower side of the array refer to the z-direction. Furthermore, the free end of the capillaries should define "front" of the array and the opposite end of the capillaries should define "rear" of the array. Finally, the perpendicular direction to the connection line between front and rear within the plane should be referred to as longitudinal direction.

Further, the array on which the capillaries are attached or fixed should not be completely impervious or opaque to light since in this way an optical measurement perpendicular to the longitudinal axis of the capillary may be complicated. The array should comprise a translucent region along the longitudinal axis of each capillary, in the following also referred to as measurement region or measurement window or measurement recess. Alternatively, the measurement region of the array may comprise a reflective and/or absorbing region or a reflecting and/or absorbing material, preferably said region or material has a low autofluorescence, preferably no autofluorescence.

For example, 24 capillaries are mechanically attached or fixed to an array according to the present invention. According to a preferred embodiment, the center to center distance of the capillaries is 4.5 mm. Said distance corresponds to the pattern of the wells in the industrial standard for 348 microwell plates (also multi well plate; 24×16 wells in a distance of 4.5 mm from center to center). As it is known that a thermophoresis measurement according to the present invention within the wells of the microwell plates is not possible, the single samples of the wells should be transferred into capillaries. Thus, an array with 24 capillaries according to the present invention (also referred to as 24 capillary array or 24 capillary chip) corresponds to a "row" (numbering 1 to 24, "landscape"-orientation) of said 384 microwell plates (cf. for example http://de.wikipedia.org/wiki/Mikrotiterplatte).

The microwell plates which are mostly rectangular mostly consist of plastic (usually polystyrene, sometimes also polyvinylchloride), for very specific uses also of glass. They contain many wells which are isolated from each other and arranged in rows and columns. The exact measures (length×width×height) amount to 127.76 mm×85.48 mm×14.35 mm according to ANSI standard upon the recommendation of the Society for Biomolecular Screening (SBS).

There are a plurality of dimensions, all on the same base area having a partly variable height: 6 wells (2×3), filling volume between 2-5 ml; 12 wells (3×4), filling volume between 2-4 ml; 24 wells (4×6), filling volume between 0.5-3 ml; 48 wells (6×8), filling volume between 0.5-1.5 ml; 96 wells (8×12), filling volume between 0.1-0.3 ml; 384 wells (16×24), filling volume between 0.03-0.1 ml, and 1536 wells (32×48), filling volume 0.01 ml. The last ones mentioned are used in the UHTS (UltraHTS).

The wells are available in different shapes: F-bottom (flat bottom), C-bottom (flat bottom having minimally rounded edges), V-bottom (tapered bottom) and U-bottom (U-shaped recess).

The standardization was up to now carried out by for example the Society for Biomolecular Sciences as ANSI standards (ANSI/SBS 1-2004, ANSI/SBS 2-2004, ANSI/SBS 3-2004, ANSI/SBS 4-2004). The distances of microwell plates are also defined in said standardizations. In particular, the distance of columns and lines adjacent to each other for 96, 384 and 1536 microwell plates is defined in said standard. In 96 microwell plates the distance between two rows or two columns amounts to 9 mm; in 384 microwell plates the distance between two rows or two columns amounts to 4.5 mm; and in 1536 microwell plates the distance between two rows or two columns amounts to 2.25 mm.

According to the invention, the array with the 24 capillaries is immersed into the 384 microwell plate, wherein the 24 capillaries may completely soak themselves within a few seconds due to the capillary forces. The array with the filled capillaries may subsequently be put in/on a carrier (in the following also referred to as tray) capable of receiving several arrays. Preferably, a tray may receive preferably up to four of the arrays according to the present invention. Then, the tray is pushed into a corresponding measurement device, for example of NanoTemper®.

By using the array of the invention together with the tray of the invention, for example 4×24=96 capillaries/samples may be measured very easily and fast, i.e., significantly fewer steps are required compared to the known method with single capillaries. For example, when filling and putting down 96 individual capillaries from a multiwell plate (1× filling+1× putting down=2 steps) 2×96=192 individual steps would be needed. When using 4 arrays, each comprising 24 capillaries (4×24=96), for filling and putting down merely 2×4=8 steps are required; the effort vis-à-vis 96 individual capillaries is thus reduced to 8/192*100%=4%, an improvement by the factor of 25. The array may be handled more easily than individual capillaries and protects the capillaries from mechanical damages and contaminations, for example fingerprints, which may disturb the optical measurements for example by their autofluorescence, which significantly increases process safety. The array prevents the individual capillaries from being mixed up and/or commutated and allows a preferably unambiguous traceability/documentation/allocation of samples to be examined to capillaries and carrier by a preferably unambiguous marking, which is advantageous for diagnostic applications and analytical applications as for example drug research or drug formulation.

The present invention alternatively or additionally relates to the tray, which serves as rack or storage box for receiving at least one, preferably two, three, four or more arrays according to the present invention. The array of the invention and the tray of the invention thus lead to a massive reduction of steps to be taken.

The array with 24 capillaries, which has exemplarily been described, is preferably not only suitable for 384 microwell plates but for example also compatible with 96 microwell plates (pattern of 9 mm); in this case for example 2 capillaries (commonly) meet 1 well of the microwell plate. The array according to the present invention may preferably not only be manually used by a person for filling and/or measuring, but may preferably also be handled automatically, for example by pipetting robots.

The array according to the present invention is preferably unambiguously marked for example in order to unambiguously assign measurement data to samples. Marking may be effected for example by means of DataMatrix Code, RFID or the like with a "unique ID", which allows to track the measurements, for example for quality control and/or diagnostic applications.

The present invention also relates to a filling station. By means of said filling station the capillaries of an array according to the present invention may preferably easily and safely be filled. Since not all users work with microwell plates, it is preferably also possible to fill the capillaries in an alternative or additional way. For example, the capillaries may be filled by means of a single channel and/or multichannel pipette, preferably manually. Said manual filling is preferably carried out from above. For smaller series of tests or preliminary tests, also parts of the array may be filled, i.e., not all capillaries of the array are filled.

In the following, further or alternative features of the present invention are exemplarily discussed.

The capillaries preferably fill themselves, i.e., only by means of capillary forces when the capillaries are immersed into a liquid. Preferably, no pumps or other active elements for filling the capillaries are required. However, it is not excluded that additional devices or elements for filling the capillaries may alternatively or additionally be used. For example, the capillaries of the array according to the present invention may also be filled by means of a pipette (see for example the discussion above regarding the filling station).

For filling by means of capillary forces it is preferred that the capillaries preferably fulfil at least one of the following criteria. The capillaries should have a small inner diameter (ID). In particular, the capillary forces depend on the inner radius/diameter of the capillary. Further, the elevation of the liquid within the capillaries also depends on the surface tension and density of the liquid. According to the present invention, different inner radii/inner diameters may be preferred for liquids having different densities. Mostly, the liquid will be an aqueous solution. Preferred inner diameters are for example in the range of 0.01 mm to 1.0 mm, further preferred in the range of 0.1 mm to 0.5 mm.

When the longitudinal axis of the capillary is parallel to gravitation and when the capillary is filled from below, the capillary forces have to draw in the liquid column against gravitation. In case for example a detergent or another substance reducing the capillary forces/surface forces is included in the solution/liquid, the capillary forces may be too weak when the longitudinal axis of the capillary is parallel to gravitation. Thus, it may be advantageous for process safety to fill the capillaries from above so that gravitation acts in the direction of the capillary forces and even supports them. It may also be advantageous to utilize the effect of the "inclined plane". For example, the longitudinal axis of the capillary may be tilted or inclined at a determined angle, preferably 45°, 60° and/or 90°, relative to gravitation (see for example the discussion regarding the filling station). Preferably, the capillaries as well as the microwell plate are tilted so that the capillary axes are preferably still aligned perpendicular to the plane of the plate bottom of the microwell plate. When only the capillaries are tilted, it may happen that, at large tilting angles, the capillaries project angularly into the wells of the microwell plate, which results in the danger that the capillaries break because they push against the walls of the wells in the microwell plate.

The microwell plates, into whose wells the capillaries are immersed, are preferably also tilted respectively against the horizontal.

Due to the limited capillary forces, only a certain "liquid column" may be put or held against gravitation. However, for an optical measurement within a capillary, for example a thermophoresis measurement, it should be preferably secured that the measuring window/the measuring region of the capillary i.e. the portion of the capillary in which the optical measurement is carried out is filled with the liquid to be measured. According to the present invention, this is achieved by the fact that the measuring portion is near the free capillary end, i.e., near the capillary end to be filled. Furthermore, the measuring window of the array is preferably aligned to the measuring region of the capillary in such a way that an optical measurement, preferably perpendicular to the plane in which the capillaries are arranged, can be carried out. It is also advantageous, in particular regarding the process safety when automating the process, when the capillary is exactly so long that it is always filled completely, for example when tilted at 90° to gravitation (=horizontal alignment). In particular, the capillaries according to the present invention are preferably horizontally aligned during a measurement, however, without being restricted thereto.

In order to allow filling of the capillaries via an end, preferably by means of capillary forces, the capillaries should have a further opening from which air may leak (otherwise simple filling is not possible). The further opening is preferably the second end of the capillary. In preferred embodiments of the array according to the present invention, the second ends of the capillaries are aligned by means of an abutment so that the first front ends are preferably in one plane and preferably on a straight line. Said abutment is preferably designed in such a way that air-vent at the second end is possible. It is preferred that the abutment allows a positioning of the capillaries without sealing the second ends. This is for example achieved by a mould incline/slope or bevel and/or step.

Preferably, the array according to the present invention or the capillaries of the array is/are not sealed after filling, i.e., the liquid in the capillaries may possibly evaporate/volatilize. Thus, the measuring window according to the present invention is preferably as far away from the positions where the vaporization/volatilization may occur that the measurement is not negatively influenced by said possible vaporization/volatilization (which may induce liquid flows).

In other words, the geometry of the capillaries according to the present invention is preferably advantageous in that the capillaries do not have to be sealed and nevertheless a reliable measurement is possible. In particular, the capillaries according to the present invention are longer or significantly longer than known capillaries in that field. Thus, according to the invention it can preferably be measured during a measuring time of for example on average 2 hours without sealing. It resulted from tests that samples vaporize at 45° C. with a liquid column loss of approximately 4 mm/hour (=2 mm/hour per end of the capillary). The measuring windows are positioned far enough from the end/s of the capillaries so that said loss due to vaporisation does not lead to the measuring window being emptied. Preferably, the capillaries according to the present invention have a length between 20 mm and 50 mm.

In order to fill a capillary by means of capillary forces, the capillary may get in contact with or be immersed into the liquid by a method according to the present invention. Said contact/immersion may cause the liquid not only to be inserted into the capillary but the capillary to be coated by the liquid also on its outer side. Said outer liquid/coating layer may lead to artefacts in optical measurements. Thus, it may preferably be avoided that the measuring window/the measuring region is coated. Thus, the array according to the invention has preferably an abutment (stop), i.e. an element which avoids that the measuring window is coated/contaminated on its outer side by the liquid to be inserted. The stop is preferably designed in a multifunctional way, as described further below, and can simultaneously serve as attachment of the capillaries to the array. Further, the stop can ensure that only the capillaries themselves may be inserted into the wells of a microwell plate, i.e., it is not possible that accidentally parts of the array or the array material reach the wells during a filling procedure and get contaminated. In a preferred embodiment of the device according to the present invention, an "adhesion topology", which is a mechanical/geometrical structure allowing the defined adhesion of the capillaries to the array material and for example additionally preventing the adhesive from spreading, works as "coating stop".

It is preferred that the depth of immersion of the capillaries into the liquid, which is preferably provided in the wells of a microwell plate, is suited to guarantee a sufficient and/or equal filling of the capillary. The array according to the present invention is preferably designed in such a way that a part or region of the capillary projects far enough in order to be able to immerse deeply enough into the microwell plates. In order to achieve a unitary depth of immersion of all capillaries of an array into the respective wells of a multiwell plate, it is further preferred that the first free ends of the capillaries to be filled lie on one line, preferably a straight line.

One advantage of the array according to the present invention is the low material consumption of the liquid in the capillaries that needs to be analysed. However, if one would need 100 µl per well for filling the capillaries or if the capillaries would always need to be filled completely ("to the edge"), the amount of material needed would significantly increase. According to the present invention, it has to be preferably ensured that the capillaries may be filled easily, i.e. in particular be immersed deeply into a microwell plate. Further, it is preferred that the liquid of the microwell plate rises above the measuring window of the capillaries. Thus, shorter capillaries are preferred and/or a measuring window near the filling end is preferred.

Microwell plates mostly have a total height of 14.4 mm 384 DeepWell Storage plates (which are often used by pharmaceutical companies) have a depth of the well of for example 11.5 mm calculated from the upper edge. 96 Deep Well Storage plates have a depth of the wells of for example up to 20 mm. The inner diameter of the well amounts to 3.8 mm, which results in a volume of 150 µl. 384 low-volume, high-bottom plates have well depths of about 5.5 mm calculated from the upper edge (depending, however, on the manufacturer).

According to the invention, it is preferred that the immersed capillaries reliably receive enough liquid by means of capillary forces even when there is for example only 20 µl of volume in the well, for example the 384 DeepWell (11.5 mm well depth, 150 µl maximum volume). Preferably, the capillaries are thus attached to the array in such a way that they may immerse down to the bottom of the well or cavity. Preferably, the device is designed in such a way that the capillaries (preferably only the capillaries) may immerse 5 mm to 20 mm into the well, preferably 10 mm to 12 mm, preferably up to 11 mm.

The capillaries may not break off when immersing into the microwell plate. This may be avoided by regions of the microwell plate and/or the base of the microwell plate pushing against edges/regions of the array before a capillary may push against the microwell plate or against the bottom of a respective well.

The measuring window/the measuring regions of the capillaries and the corresponding measuring region of the array should preferably be wide enough so that possibly low "autofluorescence" of the array material is measured even with a fluorescence measurement having optics with very high numerical aperture (NA). Thus, it is advantageous to choose an array material having low autofluorescence. Since possibly also UV measurements (for example measurement of the tryptophan fluorescence, fluorescence stimulation 280 nm) are carried out, it is further advantageous when the stimulation light cone has as little contact to the array material as possible. Preferably, the array has a recess/hole/slot in the region of the measuring window/measuring regions of the capillaries.

Dependent on the desired properties, the array according to the present invention may for example be produced with a maximum assembly of: 4, 6, 8, 12, 16, 24, 48 or 96 capillaries. A maximum assembly of 8, 12, 16, 24 or 48 capillaries, preferably 16 or 24 capillaries, particularly preferred 24 capillaries, is preferred in particular with respect to standardized microwell plates. It is preferred that the arrays according to the present invention have a maximum assembly within a range within the above limitations, for example between 4 and 96 or between 12 and 48 capillaries. Here, it is explicitly pointed out that the invention is not limited to the above-mentioned numbers. Thus, it is also possible, according to the present invention, to provide the array in such a way that it may receive more or less capillaries. Further, it is also possible that not all retaining devices on the array are equipped with capillaries. For example, it may be desirable to attach fewer capillaries to the array than the maximum assembly of the array would allow. For example, the array may be equipped with only 12 capillaries in an embodiment according to which a maximum assembly of 24 capillaries is possible.

Dependent on the desired properties, the array according to the present invention may also be equipped with different capillaries, for example with capillaries having different inner diameters or different lengths or different materials and/or different inner coating/modification. For example, the array may be equipped with capillaries having an inner diameter of 0.5 mm and 0.2 mm, for example in alternating sequences (for example 0.5 mm in uneven positions, 0.2 mm in even positions). For example, an array according to the present invention may be equipped with 24 different capillaries, for example in order to determine the optimum type of capillary for a certain application.

According to the invention, the array should have a properly defined and preferably consistent distance of adjacent capillaries. The distance of adjacent capillaries is preferably measured as center to center distance and should preferably amount to an integer multiple of approximately 2.25 mm, preferably approximately 2.25 mm or approximately 4.5 mm or approximately 9 mm between the capillaries. It is particularly preferred that the distance of adjacent capillaries, preferably the center to center distance, lies within a certain diameter starting from an integer multiple of 2.25 mm. Said diameter is preferably 0.7 mm when 96 and 384 microwell plates are used and 0.5 mm when 1536 microwell plates are used. The distance of adjacent capillaries is preferably selected in such a way that the capillaries mesh with the pattern of the wells of a microwell plate or substantially correspond thereto.

Preferably, the capillaries are continuously transparent or translucent. According to the invention it is, however, sufficient when the capillaries are optically transparent at least in the region of a measurement window. According to the invention, transparent or translucent means that a larger part of light in the wavelength ranges of 200 nm to 2000 nm is allowed to pass. Thus, it may for example be secured that fluorescence measurements may be carried out or IR light (for example from an IR laser) may be coupled into the liquid within the capillaries. Preferably, the capillaries are made of glass, for example of borosilicate glass and/or quartz glass.

The capillaries preferably have an inner diameter in the range of 0.1 mm to 1.0 mm, preferably in the range of 0.1 mm to 0.5 mm. Preferably, the capillaries have a length of 5 mm to 50 mm, preferably from 10 mm to 40 mm and preferably of approximately 32 mm.

Depending on the application, shorter or longer capillaries may be advantageous. The effects based on the length of the capillaries are chosen preferably depending on the desired application. Very short capillaries for example have the advantage that they have only a very small volume, which is advantageous with respect to the little amount of material needed (efficiency). Very short capillaries may advantageously be filled completely by means of capillary forces (when they have a correspondingly adapted diameter). If they are short enough, the capillaries do not even have to be tilted with respect to gravitation (g) since capillary forces themselves completely fill the capillary antiparallel to g. Short capillaries also have an advantage regarding space; thus, more capillaries can be placed in a limited surface.

Very short capillaries, however, also have properties which may be less advantageous for some applications. When the capillary ends are open, for example the liquid may vaporize. When capillaries are too short, the liquid may possibly vaporize too fast. Dependent on the measurement and the liquid used it may occur that the liquid is vaporized before the measurement is finished. Furthermore, vaporization streams may be too fast and/or too large dependent on the measurement, which may influence for example a thermophoresis measurement. When capillaries are too short, the immersion depth in microwell plates may also be too low. In order to balance this out, the microwell plates may be filled with liquid very highly, which may, however, be not efficient due to the high amount of material needed.

Capillaries having lengths in the range of preferably 10 mm to 40 mm, further preferred 15-45 mm, further preferred 25-35 mm, further preferred 20-40 mm, 30-50 mm, between 25 to 35 mm, between 30 and 35 mm and further preferred approximately 32 mm, for example have the advantage that they completely fill themselves also when highly viscous liquids as whole blood and cell-lysate (at an appropriate angle with respect to gravitation) are used. Complete filling is particularly advantageous since in this way high reproducibility is achieved.

When the measurement window is in addition arranged substantially in the center or exactly in the center of the capillary, a 32 mm capillary may for example be immersed 11 mm and thus far enough into the liquid of the microwell plate without the measurement window having a width of 4 mm being coated and/or contaminated by the liquid at the outer side. Preferably the measurement window in the array has a width of at least 6 mm, preferably at least 4 mm, preferably at least 3 mm so that the measurement region of a thermophoresis measurement in a capillary is far enough away from the array material. Thus, it may particularly be achieved that the array material has no or no essential thermal impact on said measurement region. In particular, decoupling of the temperature gradient from the array material may be achieved. Thus, measurement errors may be avoided.

Preferably, the width of the measurement slot or the measurement recess amounts to between 2 mm to 6 mm, preferably between 3-5 mm, and further preferred between 3.5 and 4 mm, further preferred between 3.6 and 3.8 mm. Longer measurement slots may for example unreasonably increase the amount of material needed. If for example aluminium is used as base material (array material or part of the array material), one may assume a very high thermal conductivity of the aluminium and use corresponding calculations as limitation values. In particular, when a thermophoresis measurement is carried out, a laser beam is irradiated into the liquid sample, which is placed in the glass capillary, in order to produce a temperature gradient in the sample. The aluminium of the base material may thermally interact with said produced temperature gradients. In other words, the aluminium practically extracts the heat from the temperature gradient generated by the IR laser. Calculations and measurements have shown that a distance of the array material of at least 1.5 mm to the irradiation point (measurement point) is advantageous in that the generated temperature gradient is thus no longer excessively influenced by the base material. Since, according to the present invention, the measurement window is limited by the base material preferably at two sides, it is advantageous (2×1.5 mm=3 mm) to have a measurement window with a width of at least 3 mm when the capillaries rest on both sides in order to be able to carry out uninfluenced thermophoresis measurements ("thermo-optical particle characterisation").

Furthermore, according to said embodiment, vaporization is symmetrical and as low or far away from the measurement window that even at 45° C. it may be measured in the capillaries for 1 hour without having to seal the capillaries (correspondingly longer at low temperatures). This is a big advantage regarding handling and efficiency.

The preferred capillary length mentioned above also allows it to arrange two of the capillary chips (capillary array) having 24 capillaries each practically in the plane exactly on a surface substantially corresponding to the "footprint" (ground plan) of a multiwell plate. Preferably the dimensions (length×width×height) of a multiwell plate according to ANSI standard upon recommendation of the Society for Biomolecular Screening (SBS) amount to 127.76 mm×85.48 mm×14.35 mm. If, for example, the capillary chips having 8 capillary chips each are stacked, 2 stacks with 8 capillary chips each are obtained on the footprint (of the surface) of a multiwell plate. This results in 16 capillary chips a 24 capillaries=384 capillaries; this exactly corresponds to the number of wells of a 384 multiwell plate. Hence, the capillary chips may be packed/handled in such a way that the user does not have to change his "384 multiwell plate way of thinking", i.e. retain his/her habits.

When the capillary chips are stacked in such a way (cf "stackability of the array"), a stack of 8 capillary chips including a lid also amounts to a height which may be handled by many standard "plate hotels" and laboratory robots/machines.

The capillaries preferably have an outer diameter of 0.05 mm to 2 mm, preferably 0.2 mm to 1 mm, preferably 0.2 mm to 0.65 mm. Further, it is preferred that the array is designed in such a way that also capillaries having different diameters may be attached to the array. For example, on an array according to the present invention capillaries having an outer diameter of 0.6 mm as well as 1 mm may be attached. This may in particular be achieved by an embodiment having two bridges transverse to the capillaries, as described below.

According to further preferred embodiments, the inner sides/inner walls of individual or all capillaries may be modified chemically, physically or structurally. In particular, said modification may be used to specifically change or control hydrophobic and/or hydrophilic properties and/or capillary forces. In such a way, for example surface tension and/or attachment of biomolecules and/or solutions may be changed or controlled.

According to the present invention, the inner walls of the tube-shaped structure may be modified covalently and/or non-covalently and/or by adsorption, with polymers, with silanes, biomolecules, amino acids, antibodies, proteins, nucleotides, oligonucleotides, DNA, RNA, PNA, LNA, peptides, antigens, polysaccharoses, PEG, dextran, polyacrylic acid, antifouling substances, nanoparticles, L-lysine, poly-L-lysine, aptamers, dendrimers, cells, lipids, and the like. The skilled person understands that the term "modification" or "change" also includes the process of immobilisation. The modifications or changes may also be different regarding dimensions, for example the changes may follow a pattern or gradient.

According to the invention the capillaries are mechanically attached to the array, for example, adhesively bonded and/or clamped or tucked. Alternative or additional embodiments for attaching the capillaries are: hot embossing, inserting (capillaries are inserted into the array) and fixing by a binder. The capillaries may also be injected into the array (incorporated during injection moulding). Preferably, the mechanical means for attaching the capillaries to the array are designed in such a way that also capillaries having different outer diameters may securely be attached to the same array, for example capillaries having outer diameters of 0.6 and 1 mm. Mechanical attachment/fixation of the capillaries to the array facilitates handling, in particular automated handling. Furthermore, by means of the mechanical fixation a cost-efficient and secure connection between capillary and array is achieved which is advantageous with respect to process safety. Thus, it is for example unlikely to lose or damage a capillary during use.

In order to minimize or avoid artefacts during an optical measurement, the material of the capillaries and/or the array preferably has a low autofluorescence, preferably at least in the region of the capillaries in which the optical measurement is carried out (measurement window).

Furthermore, it is preferred that the array has a high thermal conductivity (tempering of the capillaries via contact with the array material). According to further embodiments it may also be preferred that the array is made of a material having a lower thermal conductivity, for example tempering of the capillaries may be achieved via an air cushion.

It may further be advantageous for automation when the array has surfaces and/or structures for grabbing and/or movement by a robot. The array may for example have bevels on at least one side, preferably on two (opposite) sides, which may be grabbed by a corresponding fit (form fit) in a robotic grabber.

Preferably the array has surfaces (grabbing surfaces) which facilitate manual handling.

According to further embodiments it may further be advantageous to unite or combine a plurality of arrays in one tray. Preferably a plurality of arrays may be coupled to each other above each other, similar to a "stacking of Lego© bricks". Alternatively or additionally a plurality of arrays may be coupled to each other next to each other.

Preferably, the arrays may not only serve the purpose to securely fix the capillaries in a desired distance to each other, but may preferably also have a protection function for the capillaries. For example, the array may have a (foldable) frame, which may be attached in front of or above the capillaries.

According to a further embodiment, the array may also be provided with a transportation lock.

According to a further embodiment, the individual capillaries or groups of capillaries may be labelled individually, preferably by a numbering from 1 to 16, from 1 to 24, from A-P or from A-X.

According to a further embodiment, the individual arrays are coded, for example electronically and/or optically, preferably with a Datamatrix code and/or RFID. The array may also comprise a surface which may be labelled (for example classic information as batch code or life period, but also markings per hand for notices). In order to differentiate individual arrays, they may also be designed (differently) coloured. It is also possible to allocate the arrays to a company by attaching the company logo to the array.

In a further embodiment, an array is combined from different modules, for example an array with 24 capillaries may be produced by combining three arrays with 8 capillaries each to one single array.

According to further embodiments, the array may be made of a plastic with high temperature stability, which has the advantage that the array may be measured at very low and/or high temperatures (i.e. melting point curve measurement). By means of specific materials, for example high-tensile plastics, twisting of the array may also be prevented. Modelling elements may furthermore secure an exact positioning within the measurement device (for example antitwist protection).

In a preferred embodiment the array is manufactured by means of injection molding. Further exemplary manufacturing procedures are embossing, pressing, cutting, milling, printing and/or sintering.

The capillaries may be made of glass and/or a polymer and/or at least one of the elements of borosilicate glass, borosilicate-3.3-glass (for example Duran glass), quartz glass as Suprasil, Infrasil, synthetically manufactured quartz glass, soda-lime glass, Bk-7, ASTM Type 1 Class A glass, ASTM Type 1 Class B glass. The polymers may contain: PTFE, PMMA, Zeonor™ Zeonex™, Teflon AF, PC, PE, PET, PPS, PVDF, PFA, FEP and/or acryl glass.

It is particularly preferred that at least one region of the capillaries is light-transmissive for light having a wavelength of 200 nm to 1000 nm, preferably of 250 nm to 900 nm. Particularly preferred, but not limited to, is said at least one region also light-transmissive for light of the following wavelength ranges: from 940 nm to 1040 nm (preferably 980 nm+/−10 nm), from 1150 nm to 1210 nm, from 1280 nm to 1600 nm (preferably 1450 nm+/−20 nm and/or 1480 nm+/−20 nm and/or 1550 nm+/−20 nm), from 1900 nm to 2000 nm (preferably 1930 nm+/−20 nm). The skilled person understands that the transparent region(s) may also extend over the complete tube-like structure. In other words, the capillary may be transparent.

Light transmission of the segment allows carrying out measurements of luminescence/fluorescence/phosphorescence and/or optical examinations/measurements (for example interference, polarisation, absorption, dichroism, ellipsometry, anisotropy, Raman, microscopy, dark field, light diffusion, FRET) and/or manipulations of the solution/liquid and/or the gas (fluid) in the well of the tube-like structure. Light transmission can further allow carrying out fluorescence measurements. According to a preferred embodiment light transmission also enables the heating of fluids in the tube-like structure by means of electromagnetic radiation, for example light (preferably a infrared (IR) laser), preferably the heating of water and/or organic solvents.

Exemplary materials for the array are polymers, preferably polypropylene, and/or metal and/or semiconductors (for example silicium) and/or materials which preferably comprise at least one of the elements of the following group: polymer material, most preferred polypropylene, acrylnitril-butadien-styrol (ABS), polycarbonate (PC), polyamide (PA), polybutylene terephtalat (PBT), polyethylene terephthalat (PET), cyclo-olefin-copolymers (COC), polyethylene oxide (PPO), polysulphone (PSU), polyetherketone (PEK), polyetheretherketone (PEEK), polyphylene sulfide (PPS), polyoximethylene plastics (POM), polylactide (PLA) and polyvinyl alcohol plastics (PVA).

Preferred embodiments of the present invention or preferred feature combinations of the present invention are described in the following exemplary aspects:

1. An array having a plurality of capillaries arranged in the same plane and mechanically attached/fixed to the array, and wherein at least one first free end of each capillary projects from the array in such a way that the free ends of the capillaries may be inserted simultaneously into the wells of a microwell plate. Preferably the array or the capillaries of the array are used as container for samples to be examined by thermophoresis measurements.
2. The array according to aspect 1 wherein the distance between adjacent capillaries amounts to approximately 2.25 mm or an integer multiple thereof.
3. The array according to aspect 1, wherein the first free end projects 3 mm to 20 mm, preferably 10 mm to 12 mm, preferably 11 mm from the array and/or wherein the first free end projects from the array in such a way that it may be inserted 3 mm to 20 mm, preferably 10 mm to 12 mm, preferably 11 mm into a well of a microwell plate. According to the invention, preferably only the free capillaries should project from the array in such a way that it is secured that when immersing the free ends into the wells of a microwell plate in fact only the capillaries are inserted into the wells.
4. The array according to any one of the preceding aspects, wherein the capillaries are attached/fixed to the array in such a way that a second end of the capillaries is open in such a way that air may leak, preferably when the first free end is filled with a liquid or is immersed into a liquid in order to be filled.
5. The array according to any one of the preceding aspects, which comprises on at least one side, preferably on both sides, one/a plurality of gripping surface(s) and/or positioning guide(s) for an automatic handling.
6. The array according to aspect 5, wherein the positioning guide is preferably designed for an automated seizing or guiding and comprises preferably at least one tapered section, preferably two tapered sections.
7. The array according to aspect 6, wherein the tapered section(s) comprise(s) at least two sloping surfaces approaching each other or running away from each other and wherein, preferably, the tapered sections are differently orientated, for example cross to each other.

8. The array according to any one of the preceding aspects, wherein the array comprises at least two bridges which are preferably substantially parallel to each other and which extend preferably substantially transversely to the longitudinal axis of the capillaries, and are preferably spaced apart from one another. According to a preferred embodiment the front bridge may also serve as an abutment with a microwell plate in order to insert the capillaries, preferably only the capillaries, into the wells of a microwell plate in the desired predetermined length.

9. The array according to any one of the preceding aspects, wherein the capillaries are attached/fixed to the array preferably each on at least two points or sections, wherein preferably one point is on the first bridge and one point is on the second bridge.

10. The array according to any one of the preceding aspects, wherein the array comprises a rear bridge comprising preferably an abutment in order to cooperate with the capillaries.

11. The array according to any one of the preceding aspects, wherein the array comprises a measurement recess so that the capillary may be screened or illuminated by means of light from a light source which radiates light substantially perpendicular to the common plane, preferably in a central region between the first and the second end of the capillary. Preferably, the measurement recess should be large enough to be able to carry out an optical measurement on the one hand and/or large enough that the actual measurement region of the capillary is far enough away from the material of the array in order to avoid or minimize a thermal impact of the measurement region by the array. Preferably, the measurement recess has a width between 2 mm-6 mm, preferably between 3-5 mm, and further preferred approximately 4 mm 12. The array according to aspect 11, wherein the measurement recess is arranged between both bridges.

13. The array according to any one of the preceding aspects, wherein the array comprises a tempering region, preferably two tempering regions, which enable preferably an individual or simultaneous tempering of one or more capillaries.

14. The array according to aspect 13, wherein the tempering region is arranged between one of the bridges and the rear bridge and between one of the bridges and the free end.

15. The array according to any one of the preceding aspects, wherein the first free end of each capillary projects from the array by projecting from one of the bridges, in particular from the outer bridge facing the free end.

16. The array according to any one of the preceding aspects, wherein the first free end of each capillary projects from the array or is freely spaced apart therefrom.

17. The array according to any one of the preceding aspects, wherein outer regions of the array, preferably the handle regions, are outwardly spaced apart from a fictive line (A) connecting the first free ends of the capillaries, preferably by 2 mm, preferably in such a way that the capillaries do not cut the fictive line (A).

18. The array according to any one of the preceding aspects, wherein the microwell plate is a standard 96, 384 or 1536 microwell plate.

19. The array according to any one of the preceding aspects, wherein the array is equipped with 4, 6, 8, 12, 16, 24, 48 or 96 capillaries.

20. The array according to any one of the preceding aspects, wherein the capillaries have an inner diameter in the range of approximately 0.01 mm to approximately 1.0 mm, preferably in the range from 0.1 mm to approximately 0.5 mm and/or a length of approximately 5 mm to approximately 50 mm, preferably from approximately 10 mm to approximately 40 mm and preferred approximately 32 mm 21. The array according to any one of the preceding aspects, wherein the mechanical attachment/fixation between capillary and array is at least one combination from the group consisting of: glue, clip attachment, clamping, pressing.

22. The array according to any one of the preceding aspects, wherein the array comprises one or more cut-outs for exact positioning and guiding of the array.

23. The array according to any one of the preceding aspects, wherein the array is preferably produced by means of injection moulding, embossing, pressing, cutting, milling, printing and/or sintering.

24. The array according to any one of the preceding aspects, wherein the array may be clearly marked, preferably by means of at least one of the following procedures: labelling, colouring, barcode, 2D barcode, DataMatrix Code, RFID.

25. The array according to any one of the preceding aspects, wherein the array and the capillary are produced in one piece.

26. The array according to any one of the preceding aspects, wherein the inner diameter of at least one of the plurality of capillaries, preferably of all capillaries, diminishes with respect to the first free end and/or to the second end of the capillary.

27. A kit having an array according to any one of the preceding aspects and a tray for receiving at least one array, preferably for receiving a plurality of arrays.

28. The kit according to aspect 27, wherein the tray comprises devices, preferably protrusions, for positioning the array(s).

29. A method for filling a plurality of capillaries in an array, in particular according to any one of the preceding aspects, wherein the plurality of capillaries are filled simultaneously by means of capillary forces, by inserting the first free ends of the capillaries simultaneously into the wells of a microwell plate.

30. The method of filling a plurality of capillaries in an array according to any one of the preceding aspects, wherein a plurality of the plurality of capillaries are filled simultaneously by means of a multichannel pipette via the first free ends.

31. The method of filling a plurality of capillaries in an array according to any one of the preceding aspects, wherein the plurality of capillaries are filled one after another by means of a single-channel pipette via the first free ends.

32. The method of filling a plurality of capillaries according to any one of aspects 29 to 31, wherein the array and/or the capillaries are aligned diagonally between a horizontal and vertical position or vertically with respect to gravitation.

33. The method according to any one of aspects 29 to 32, wherein the method is carried out by using a kit according to any one of aspects 27 or 28.

34. The method according to any one of aspects 29 to 33, wherein the method is conducted in an automated way.

35. The method according to any one of aspects 29 to 33, wherein the method comprises at least one of the following steps which are conducted in an automated way:
   1. removing an array according to any one of aspects 1 to 26 from a package/stack
   2. transporting the array to a filling position
   3. filling the array 4. transporting the filled array to a tray/measurement device
5. positioning on the tray/in the measurement device
6. conducting a measuring procedure
7. removing the array/tray from the measurement device and transportation to a storage container (e.g. rubbish bin or intermediate storage).
36. A filling station for filling the capillaries of an array according to any one of aspects 1 to 26, wherein the filling station comprises a mounting for the array and the array is preferably tilted at an angle between 0° to 180° with respect to gravitational force.
37. The filling station according to aspect 36, wherein the mounting is adjustable so that the array may be aligned/tilted in a desired angle with respect to gravitational force.
38. The filling station according to aspect 36 or 37, wherein the filling station comprises a mounting for receiving a microwell plate, wherein the microwell plate may be aligned in a tilted way with respect to gravitational force, preferably may be tilted/aligned at the same angle as the array.
39. A tempering device for tempering the capillaries of an array according to any one of aspects 1 to 26, wherein the tempering device comprises a tempering body with tempering partitions being spaced apart from each other, and the array may be laid onto the tempering body in such a way that at least one, preferably a plurality of tempering partitions lie between the capillaries.
40. The tempering device according to aspect 39, wherein the capillaries are preferably heated/cooled by means of a tempered air cushion between the tempering partitions and the lid.
41. The array according to any one of the preceding aspects 1 to 26, wherein the array comprises stacking elements preferably at least one tooth projecting downwards from the lower side of the array and at least one recess on the upper side of the array for receiving a respective tooth.
42. The array according to aspect 41, wherein the distance (b) between two capillaries of two arrays stacked on top of another amounts to substantially 4.5 mm.

BRIEF DESCRIPTION OF THE FIGURES

In the following, preferred embodiments of the present invention are described in detail with respect to the Figures. The Figures show:

FIGS. 1A and 1B a side view and a top view of an array with 24 capillaries attached thereto;
FIGS. 1C and 1D schematic details of preferred abutments of the capillaries at the array;
FIG. 2A a perspective view of the array of FIG. 1;
FIG. 2B a partial view of a handle portion of the array of FIG. 2A;
FIG. 2C details of a gripping surface for handling systems/robots;
FIG. 5 method steps for filling arrays of the invention;
FIGS. 7A and 7B a perspective view of an alternative embodiment of the array, here exemplarily according to FIG. 6, having inter alia an abutment in the form of a recess or gap;
FIG. 7C a preferred detail of a gripping surface for handling systems/robots, here exemplarily for the embodiment according to FIG. 6 or 7A and B;
FIG. 8 a schematic perspective example for automated handling, wherein
FIG. 8A shows an end of an array with a handle portion and FIG. 8B shows said ends with a grab of a handling system and FIG. 8C shows a complete view of an array having engaged grabs;
FIGS. 9A to 9D a tempering device by means of which the capillaries of an array according to the present invention may be tempered, wherein
FIG. 9A shows the array separated from the tempering device,
FIG. 9B shows the array engaged with the tempering device,
FIG. 9C is a detailed view of FIG. 9B
and FIG. 9D shows a sectional view along the line A-A of FIG. 9C.

DETAILED DESCRIPTION OF PREFERRED EMBODIMENTS

Figure 3A:
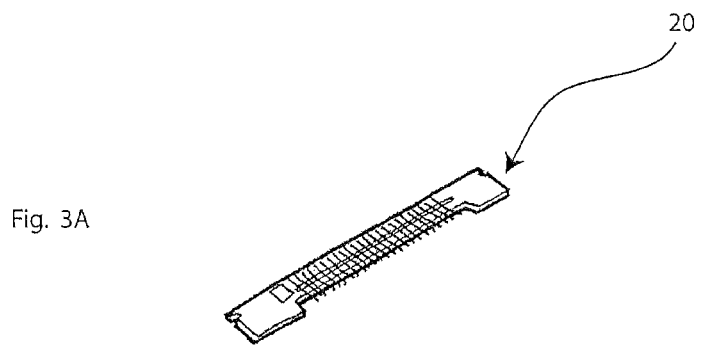
FIG. 3A a further schematic perspective view of the array of FIG. 2A.

FIG. 1B schematically shows an exemplary embodiment of an array 20 according to the present invention in a top view. 24 capillaries 1 with a consistent distance of about 4.5 mm are attached to the array in a common plane, wherein the common plane lies parallel to or in the paper plane. In particular, the common plane is visible in the side view of FIG. 1A. The array has substantially two, preferably approximately parallel mounting struts 21, 22. Preferably, each capillary 1 is attached/fixed to both mounting struts, i.e. each capillary is mounted to the array at least at two points 9, 10 being spaced apart from each other, which enables a secure mounting. Preferably, both mounting struts 21, 22 are being spaced apart from each other. Preferably, the measuring slot/the measuring window 2, which enables light to be transmitted through the individual capillaries perpendicular to the common plane, is positioned between both mounting struts. For example, the measuring slot/measuring window 2 allows to conduct optical measurements, for example fluorescence measurements, preferably microscale thermophoresis measurements.

Preferably the measuring slot or the measuring window 2 is arranged in the center regarding both ends of the capillary 1, i.e., the measuring window and the capillary length are preferably symmetrical. For example, the array according to the invention is used for thermophoresis measurements. Thermophoresis is a transportation process for particles or biomolecules, i.e., said transportation process may also be influenced by different transportation processes. Other transportation processes are for example flows in the liquid of the capillary which may arise due to vaporization of the liquid at the capillary edges. Thus, for example at least two liquid flows may exist, wherein particle flows in the direction of the capillary ends arisen due to vaporization, in principle may have a negative impact on thermophoresis measurements. If the measurements are conducted preferably substantially in the center or exactly in the center of the capillary (symmetry!), both opposite vaporization flows may add to zero, which enables an undisturbed thermophoresis measurement.

Also regarding tempering of the capillaries or the solution in the capillaries, a measuring window positioned exactly in the centre is advantageous, since in this way also symmetry effects may be used. This is also advantageous regarding filling. No matter whether it is filled from "the front" (=free end) or from "the rear" (end which projects into the array), the liquid always has to cover the same distance to the measuring window, i.e., both filling methods may be compared to each other. During filling and the respective first coating of the capillary walls with the liquid, often biomolecules/particles stick/adhere to the capillary walls, i.e., on the way to the measuring window one possibly "loses" biomolecules/particles freely swimming in the solution. If the distance is equal, on average the same amount of biomolecules/particles is lost, which is why the symmetry is also advantageous regarding filling.

At the (in the drawings upper and lower) ends of the mounting struts 21, 22 preferably handle portions 3 are present. On the one hand said handle portions allow grabbing the array by a user and furthermore, strongly connect both mounting struts to each other. Furthermore, the handle portions 3 may also be designed in such a way or have respective devices, that an automated grabbing of the array is enabled or facilitated. In particular, reference number 4 provides a device or guidance for an automated grabbing or guiding. The handle portions 3 furthermore preferably comprise a labelling region 5 on which information may be applied in writing or machine-made.

The array is designed in such a way that the capillaries may be filled from one side (in FIG. 1B the right side, in FIG. 1A the side facing the viewer). Said side is also referred to as 'front' side. The opposite side of the array (in FIG. 1B the left side or in FIG. 1A the not visible side facing away from the viewer) is also referred to as "back side" or "rear" side. Corresponding terms are used with regard to the capillaries arranged in the array.

In the following, both ends of a capillary 1 are referred to as first free or front end 11 (right end in FIG. 1B) and as second or rear end 12 (left end in FIG. 1B). The first front ends preferably project approximately 11 mm over the array, more precisely over the front (right) mounting strut 22 of the array, so that said ends may simultaneously be inserted into the wells of a microwell plate in such a way that filling of the capillaries is made possible (cf. for example FIG. 5-2*a*). Preferably, a plurality of, preferably all front ends 11 of the capillaries 1 are on a common (front) line A (cf. FIG. 1B), which allows that the capillaries may simultaneously be inserted equally far into the wells of a microwell plate. Preferably, line A is parallel to a virtual connection line between the upper front end of the handle 3 and the lower front end of the handle 3. Preferably, line A lies on said virtual connection line.

Furthermore, the handle 3, in particular the front section or the front end of the handle 3 (right in FIG. 1B) may serve as abutment, which for example secures that the front ends 11 of the capillary 1 are immersed into the wells of a microwell plate at a desired or predetermined immersion depth, i.e., the handle 3 in its function as abutment may avoid that the front ends 11 of the capillaries 1 hit the bottom of the wells of a microwell plate and are thus not damaged. For example, the distance between the front ends 11 of the capillaries and the line A amounts to 2 mm. Additionally or alternatively also the front (right) mounting strut 22 of the array 20 may serve as such abutment.

The array according to the present invention preferably has at least one abutment which is designed in such a way that the abutment comes into contact with (abuts on) one outer side of a microwell plate when the capillaries are filled (immersing the capillaries into the wells filled with liquids), which secures that only the capillaries and no other material of the array is inserted into the wells. In other words, according to the invention only the capillary material comes into the interior of the wells when immersing the capillaries into the wells of the microwell plates, which avoids undesired contamination of the liquid by array material.

The array preferably comprises a (rear) abutment 13, to which the rear ends 12 of the capillaries may be aligned. The abutment 13 is preferably provided on a third strut 23, which is, preferably approximately parallel, provided on the struts 21, 22, further preferably in the region of the rear of the array. Equally long capillaries may thus be aligned to abutment 13, which runs preferably parallel to the mounting struts. Thereby, it may advantageously be achieved that the first front ends 11 of the capillaries 1 lie on a common straight line (parallel to the dashed line A in FIG. 1B).

A slot 6 is provided between the abutment 13 or the rear strut 23 and the (left) rear mounting strut 21 according to said embodiment. Said tempering slot 6 enables an individual or a common tempering of the capillaries by means of for example tempered air (heated or cooled), guided through the tempering slot 6. Alternatively or additionally also heat conducting material may be present in the tempering slot 6, which is being tempered via tempering elements in the measuring device and connected to the capillaries in a heat conducting way. Preferably, the region between the bridge 22 and the capillary end 11 may additionally be used for the tempering of the capillaries. Additionally and/or alternatively the region between the bridges 21 and 22 may for example be used for the tempering of the capillaries.

In order to allow a filling of the capillaries 1 at the front end 11, the abutment 13 and the rear end 12 of the capillaries are preferably not in fluid-tight contact. In the shown embodiment an air-vent slot 7 is present, by means of which the air in the capillaries may leak when filling the capillaries. Said slot may for example be achieved by providing a mould incline 14 and/or step 15. This is exemplarily shown in the schematic details of FIGS. 1C and 1D. The air-vent slot may for example also be designed in such a way that it consists of a small air gap between abutment 13 and rear capillary end 12, for example the abutment does not have to be oblique in this case.

Each capillary 1 has an individual labelling 8 at the abutment, here at the strut 23 forming the abutment.

FIG. 2 shows a perspective view of a respective array. FIG. 2B shows the detail of a handle portion 3 with a device or guidance for automated gripping or guiding. Said device or guidance is preferably designed in a tapered way and has two surfaces 4*a*, 4*b* running obliquely outwards, i.e. facing away from the array, towards each other. Furthermore, the device 4 preferably comprises front and/or rear abutments 4*c* or 4*d*. Said abutments run preferably obliquely or bent towards each other (tapered), in particular from outwards to inwards, or in the direction of the capillaries. An inner abutment 4e, i.e. arranged from outwards in direction to the array or the capillaries, may also be provided. Preferably two abutments 4c, 4d and/or 4e each are provided, which are arranged substantially symmetrically preferably with regard to the tapered design of the surfaces 4a, 4b. FIG. 2C shows a sectional view A-A of a detail of the guiding device 4 according to FIG. 2A.

Preferably, the array is designed in a stackable manner. In particular, the arrays may lie on top of each other or be stacked without the capillaries being damaged or contaminated. This may for example be achieved by a suitable "thickening" of the array, for example in the section of the handle portion 3. In order to allow a secure positioning in the stack, preferably stacking elements are provided (not shown; cf., however, FIGS. 11-15), which for example allow positioning and sufficient spacing apart.

For example, at the lower side of an array at least one stacking element, preferably in the form of one or more teeth is provided. In order to prevent the stacked arrays from shifting, it is further preferred that respective recesses are provided on the upper side of an array, wherein the tooth or the teeth engage with the corresponding recesses of the array lying below, when stacked. Preferably, the teeth and recesses are designed similar to plastic building blocks, for example Lego®. Furthermore, it may be advantageous to design the shape and/or size of the teeth differently in order to secure that two arrays are stacked on top of each other only in one position. Furthermore, instead of the teeth, recesses may be provided below at the array and above on the array respective teeth may be provided. Further exemplarily and preferably the arrays are designed in such a way that the distances of the corresponding capillaries 1 of two adjacent arrays in the stacked condition, as described above, amount to approximately for example 4.5 mm or another multiple of 2.25 mm. In this way, the capillaries of the stacked arrays may be immersed and filled preferably simultaneously.

FIGS. 7A and 7B show a perspective view of an alternative embodiment of the array as well as a corresponding detail. Said array has an abutment 13' in the form of a recess or pocket, which may be used also in the other embodiments. The remaining features correspond to those which have been described in relation to the other embodiments. Here, the capillaries 1 for example push against a rear abutment, as described above and for example explained in relation to FIGS. 1C and 1D or for example a small air gap is provided between capillary end 12 and abutment 13'. The capillaries 1 are additionally positioned in a pocket or recess, wherein preferably one pocket for each capillary is provided. Said embodiment preferably allows, besides the advantages mentioned above, that not only air may leak from the capillary but that possibly additionally leaking liquid is collected and preferably soaked back into the capillary. In this way it is preferably prevented that leaking liquid runs from one capillary into adjacent capillaries. Preferably, an undesired "cleaning" of the capillaries may be complicated or even prevented.

Figure 3B:
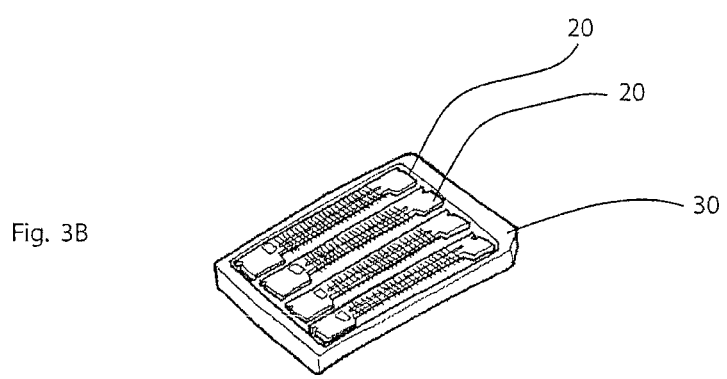
FIG. 3B four arrays of the invention in an tray according to the present invention.
Figure 3C:
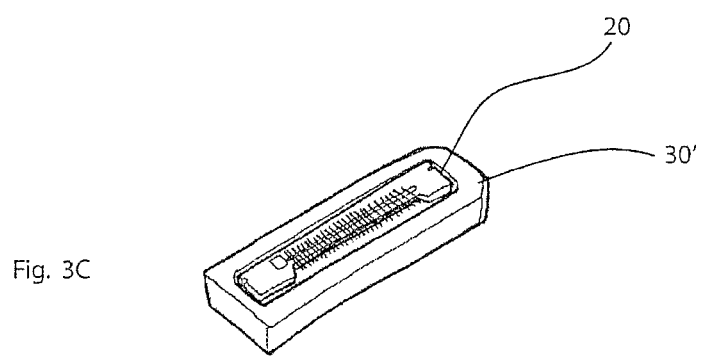
FIG. 3C an array of the invention in a tray of the invention according to a further embodiment.

FIG. 3A shows a further schematic perspective view of the array of FIGS. 1 and 2A. In FIG. 3B it is exemplarily shown how a plurality of, here four, arrays 20 of the invention are arranged in a tray 30 of the invention. FIG. 3C shows a further tray 30' of the invention which is designed to receive a single array 20. Tray 30 or 30' is designed in such a way that it may receive one or more arrays 20.

In order to achieve this, the tray preferably comprises one or more recess(es) and/or further mechanical means, as for example protrusions or clamping devices. Said protrusions or clamping devices match with the geometry of the array and preferably allow a secure, anti-slip positioning of the array(s) on the tray.

Figure 3D:
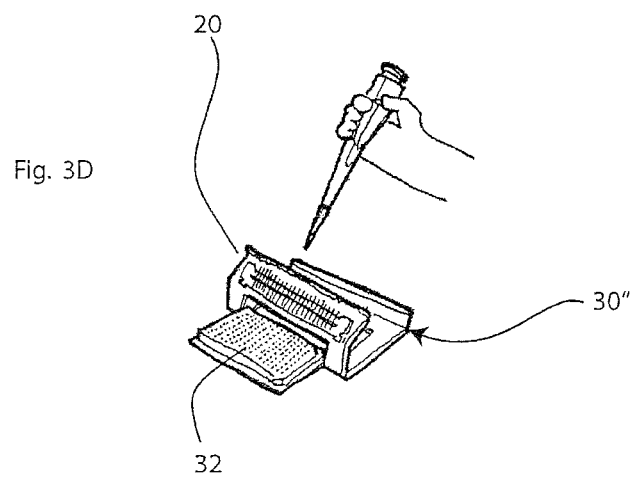
FIG. 3D a filling station of the invention with an obliquely attached array, whose capillaries are manually filled by a pipette.

FIG. 3D shows a filling station 30' according to the present invention with an array 20 according to the present invention. Further, the filling station 30" is preferably designed or aligned in such a way that an inclined positioning of the array 20, for example at 45° to the horizontal, is achieved. In doing so, for example manual filling may be facilitated. The preferred advantages of such a tilting of the array 20 and/or the capillaries with respect to gravitational force is described further below with regard to FIG. 10. Furthermore, the filling station 30" is preferably designed in such a way that a multiwell plate 32 may be received and arranged with respect to the array. Hence, manual filling of the capillaries may be facilitated.

FIGS. 4A to 4D show examples for the mechanical attachment of individual capillaries 1 to the arrays according to the present invention, however, without being restricted thereto. For example FIG. 4A on the left shows a capillary 1, which is attached to the array by means of a two-part clip. In the shown embodiment the two-part clip comprises two L-shaped elements 41, 42 substantially projecting from the array, which attach the capillary 1 to the array. Preferably at least one of the elements 41, 42 is so flexible that the capillary may be pressed into the intermediate space 43 between the L-shaped elements, i.e., at least one of the L-shaped elements 41, 42 flexibly moves outwards to the side, when the capillary is pressed into the intermediate space and preferably springs back again when the capillary is positioned in the intermediate space 43. This may preferably be supported by providing a bevel 44 on at least one of the elements 41, 42.

Figure 4A:
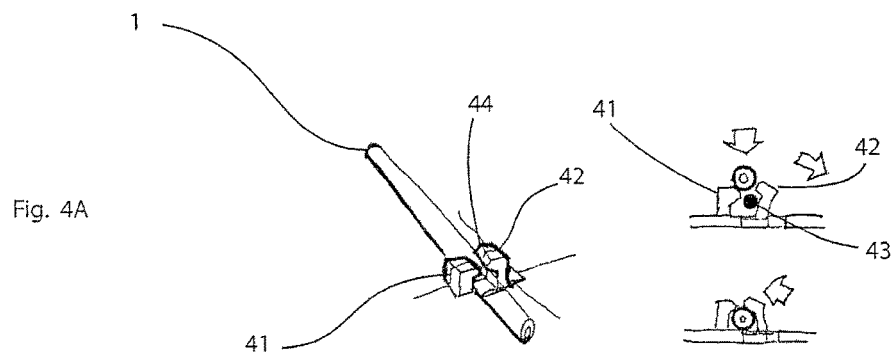
FIG. 4A to 4D examples for the mechanical attachment of the capillaries at the array of the invention.
Figure 4B:
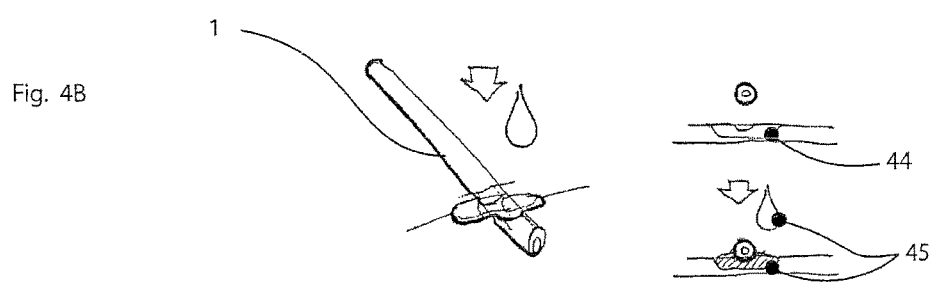

FIG. 4B shows a further embodiment of the invention for attaching the capillary 1 on the array by means of adhesion. Preferably, the array comprises a recess 44 or notch 44 which may receive adhesion 45 and/or the capillary 1. In the shown embodiment, the depth of the recess is smaller than the diameter of the capillary so that the adhered capillary projects (upwards) from the array.

Figure 4C:
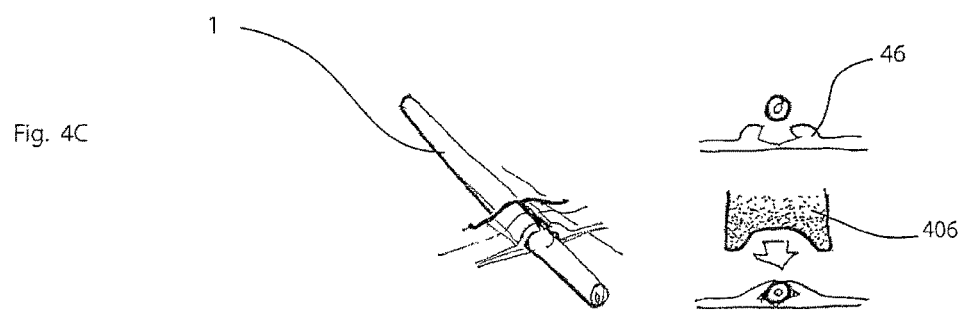

FIG. 4C shows a further embodiment of the invention for attaching the capillary 1 on the array by means of embossing or hot embossing. Preferably at least one element 46 is provided which gets plastically deformed so that it fixes the capillary after inserting a capillary 1. This may be achieved preferably by means of a respective tool, for example a stamp 406, which may also be designed as hot embossing stamp.

Figure 4D:
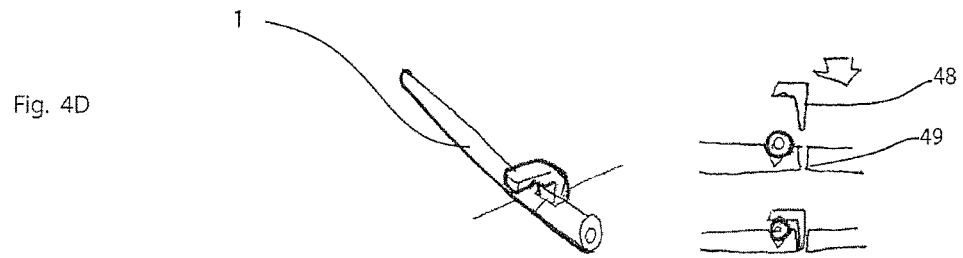

Finally, FIG. 4D exemplarily shows the attachment of the capillary 1 to the array by means of an additional mounting piece 48. Mounting piece 48 is preferably designed as an element which is separated by array 10 and is a substantially angle-shaped or L-shaped. For example a U-shape or other geometries are possible. The array or bridge is provided with a respective receiving element, here opening 49. The mounting of mounting piece 48 at the receiving element 49 may be achieved form-fit and/or by frictional connection. The shape of the mounting piece allows an inserted capillary to be embraced and be fixed to the array.

Preferably the mounting means, in particular as described above, are designed in such a way that they, possibly together with the bridge, substantially embrace the individual capillary along its periphery. Thus, preferably a barrier may be formed which prevents the liquid which got onto the outer side of the capillaries when filling the capillaries from ending up in the measurement region. The barrier may be mechanically (almost complete embracement) and/or physically (only little slot or free space so that for example due to surface tension within the times of use, for example up to 5 days, no liquid may leak).

FIG. 5 shows preferred method steps for filling arrays according to the invention as well as the use of arrays and trays according to the invention. Here, in a first step according to FIG. 5 a multiwell plate is filled with sample liquid. This is preferably conducted by a filling robot, as also known in the prior art.

Subsequently, according to step 5-2, the capillaries arranged in the array according to the invention are filled. This is for example carried out by simultaneous immersing of all capillaries of at least one array into wells of the microwell plate according to step 5-2*a*. A stacked arrangement of a plurality of arrays, as described above, allows simultaneous filling of the capillaries of a plurality of arrays. Here, the array is advantageously preferably designed and/or dimensioned in such a way that positioning of the array and thus of the capillaries relative to the microwell plate is facilitated, for example by given abutments, for example of the handle portions 3 at the microwell plate. Preferably, also an adaptor or a filling aid may be provided, schematically illustrated in FIG. 5-2*a*, which supports and facilitates immersion and filling of the capillaries. The array according to the present invention thus allows a semi-automatic, simultaneous filling of a plurality of capillaries, for example of 24 capillaries.

Figure 10:
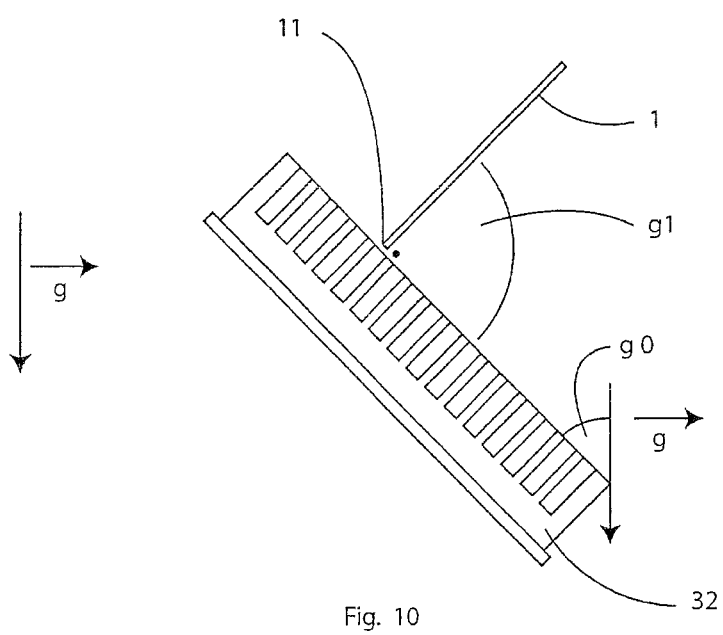
FIG. 10 tilting of a capillary and an array, wherein the filling of the capillary is explained with respect to weight.

Preferably, the filling aid prevents the capillaries from being damaged. Preferably, the filling aid is designed in such a way that the capillaries and the microwell plate are aligned preferably in a predetermined angle relative to the gravitational direction, in order to support the filling of the capillaries. For example FIG. 10 illustrates the tilting of the microwell plate 32 and the capillaries 1 with respect to gravitational force. Preferably the microwell plate and/or the capillary is aligned in angles of about 0°, about 30°, about 45°, about 60°, about 90° or about 180° with respect to gravitational force g. Preferably, said alignment/tilting is carried out by the filling aid in such a way that the longitudinal axis of the capillaries is substantially perpendicular (see angle g1) to the ground/bottom surface of the microwell plate. For example the microwell plate is aligned by the filling aid in such a way that its ground/bottom surface is aligned in an angle of 30° with respect to gravitational direction (see angle g0), preferably the capillaries/capillary arrays are aligned by the filling aid in such a way that they form an angle of 60° with respect to gravitational direction. Preferably, the microwell plate 32 and the capillaries 1 are aligned by the filling aid in such a way that breaking off of the capillaries when being immersed into the microwell plate is avoided. Preferably, the microwell plate is aligned vis-à-vis the capillaries in such a way that the longitudinal axis of the capillaries is aligned parallel to the walls of the wells in the microwell plate. Preferably, said inclination with respect to the gravitational direction facilitates the filling of the capillaries, since the capillary forces do not have to work against the full gravitational forces when being inclined ("principle of the inclined plane"). For example, the inclination of the microwell plates and the capillaries may depend on the liquid to be sucked in, for example the microwell plate may be aligned in a larger angle relative to the gravitational direction when liquids having many detergents are used, in order to avoid leakage of the liquids from the wells. For example, the ground/bottom plane of the microwell plate may be aligned in an angle of 0° relative to gravitation or for example also in an angle of 180° relative to gravitation (microwell plate is upside down) in order to guarantee the filling of the capillaries with very viscous liquids or liquids which have marginal capillary forces.

Alternatively, the capillaries may be filled by pipetting, as for example described in relation to FIG. 3D or 5-2*b*. Here, the array of the invention is particularly advantageous since it allows a secure filling, in particular by suitable alignment and arrangement of the capillaries. Thus, in particular, simultaneous filling of a plurality of capillaries is advantageously allowed.

Alternatively, as described further below, the array according to the present invention allows an automated filling of the capillaries.

In a preferred subsequent step 5-3 the array or the arrays are deposited or positioned on a tray according to the present invention. Subsequently, the tray with the array(s) is inserted into an analysis device, according to step 5-4. Depending on the kind of analysis device the arrays may also be inserted directly, i.e. without tray. However, using a tray proves to be advantageous, in particular regarding handling and process safety.

After analysis, the tray is removed from the analysis device, possibly intermediately stored, for example for later comparative measurements, and subsequently emptied, according to step 5-5. The tray may then be re-used. The arrays are preferably deposed of.

Figures 6A, 6B:
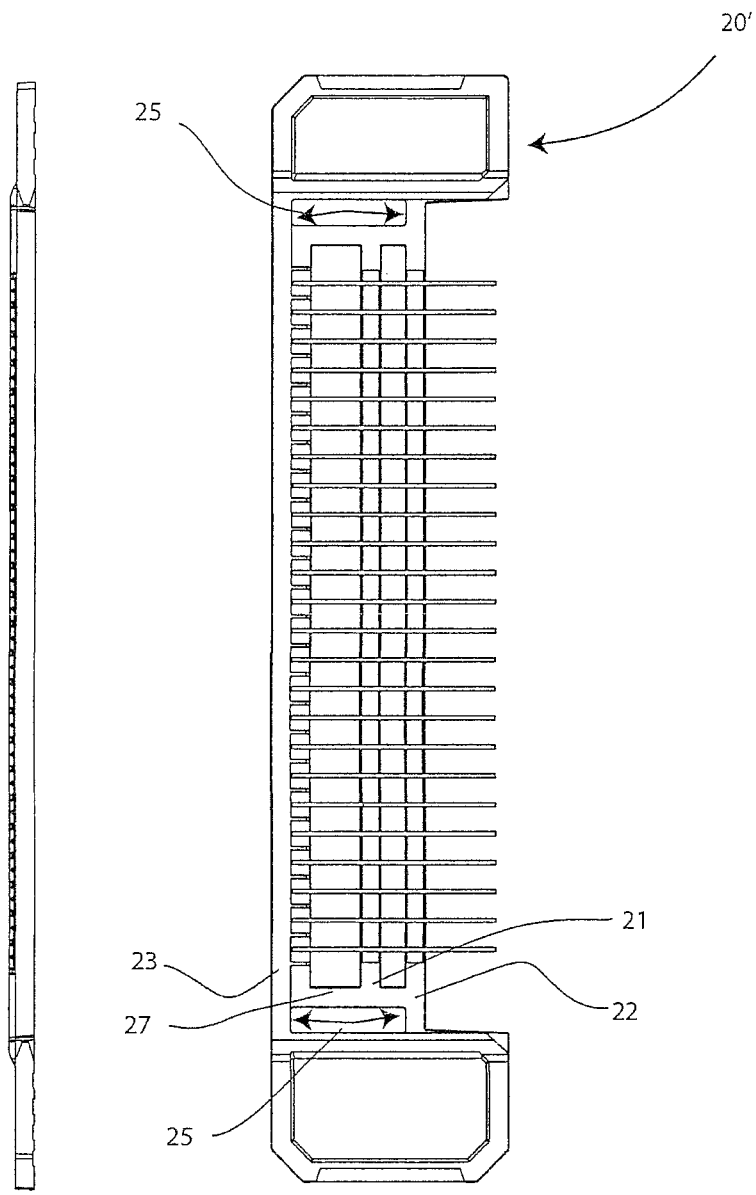
FIGS. 6A and 6B a side view and a top view of an alternative array of the invention with 24 capillaries attached thereto.

FIG. 6B schematically shows an exemplary embodiment of an array 20' of the invention in a top view, FIG. 6A in a side view. The array 20' substantially corresponds to the array described in connection with FIGS. 1 and 2. Thus, subsequently only the differences are discussed, wherein the differentiating features of the embodiments may be preferably provided also in the respective other embodiment. Preferably, for example the recess-shaped abutment 13' according to the embodiment shown in FIGS. 6 and 7, as already described above, may also be provided in the embodiment shown in FIGS. 1 and 2. Conversely, this also applies for the abutment according to the embodiment shown in FIGS. 1 and 2, which may also be provided in the embodiment shown in FIGS. 6 and 7. Further, the features described hereinafter, separately or in combination, may also be provided in the other embodiments or be replaced or completed by the features provided in the other embodiments.

The array according to FIG. 6 preferably comprises at least one cut-out or opening or recess 25, as shown preferably two. The cut-outs 25 are preferably designed oblong and extend approximately parallel to the capillaries 1. Preferably, the cut-outs 25 are arranged between handle portion 3 and the capillaries 1. They may be limited by the handle portion 3, the bridges 21, 22 and/or 23 as well as a further limitation bridge 27 substantially extending transversely to the bridges 21, 22 and/or 23 and is arranged preferably between cut-out 25 and the capillaries 1.

The cut-out preferably allows exact positioning and alignment of the array, for example when filling it semi-automatically or automatically and/or when arranging it on a tray according to the present invention. Exactly aligned protrusions grasp into said cut-outs, which allows an exact positioning or alignment of the array. Such protrusions or projections may be provided on a filling accelerator, a tray and/or a grab of a robot/handling device.

A further preferred feature is the formation of a depth stop by cut-outs 25. This may be advantageous when immersing into microwell plates. In particular, a guiding element, for example a cylindrical bolt (not shown), may engage with these cut-outs. So, the array may only be shifted around the region of or along the free cut-out (cf. array in FIG. 6B). Such a guiding element may be provided on a filling aid and/or a grab of a robot/handle device. The cut-outs thus advantageously allow a guiding and/or positioning in the longitudinal direction of the capillaries arranged on the array and/or in cross direction of the capillaries in their arrangement plane. Preferably, the cut-out is not designed as constant cut-out but as recess. In this way, for example a guiding and/or positioning perpendicular to the arrangement plane of the capillaries may be allowed. In this case, at least 1, 2, or 4 cut-outs 25 may be provided. When more than two cut-outs designed as recesses are provided, two cut-outs each on opposite sides of a handle portion 3 may be arranged. Thus, an advantageous, multidimensional guiding and/or positioning may be achieved.

A further advantage of the arrays according to the present invention is the possibility of automation. In particular, the arrays of the invention preferably have devices/grab surfaces 4 allowing the array to be handled automatically, for example with pipetting robots or other automated devices/grabs. Thereby, the complete filling procedure may be completely automated. A preferred embodiment of the guiding or grabbing means 4 was already described above. Such means 4 particularly facilitate grabbing for example by means of a handling device. Preferably said means are arranged on opposite outer sides of the array, preferably on longitudinal sides (sides extending transversely to the longitudinal axis) of the side of the handle portions 3 facing outwards. The skilled person will, however, know that also different positions are possible.

The grabbing means, for example as described above, are designed in such a way that or particularly allow that the array may be positioned securely and centred in a grab. For example may the tapered surfaces 4a, 4b, 4c, 4d support the automated alignment or the automated centering in the horizontal as well as the vertical axes. Even if the array is not completely strongly grabbed, it may not easily fall out of the grabs (tolerance zone).

The grabbing means further allow grabbing of the array from a stack of arrays, from a packaging, from a surface or from a device. Here, it is merely required that there is enough space at the narrow side for the grabs to grab at the grabbing means. The handle/grabbing means are preferably designed in such a way that they may be grasped with a combined grab which is able to carry out different handling steps.

FIG. 8 exemplarily shows a respective grab of a robot or handling system which has a geometry corresponding to the grabbing means and engages with the grabbing means. The grab preferably has surfaces which correspond to surfaces 4a, 4b, 4c, 4d and 4e and which may engage with these surfaces, in particular in order to allow a secure grabbing and a secure positioning and handling. FIG. 8 shows a schematically perspective example for automated handling, wherein FIG. 8A shows an end of an array with a handle portion 3 and FIG. 8B shows said end with a grabber of the handling system which engages with the grabbing means 4 of the handle portion 3. FIG. 8C shows a complete view of the array with engaged grabbers.

Figure 9A:
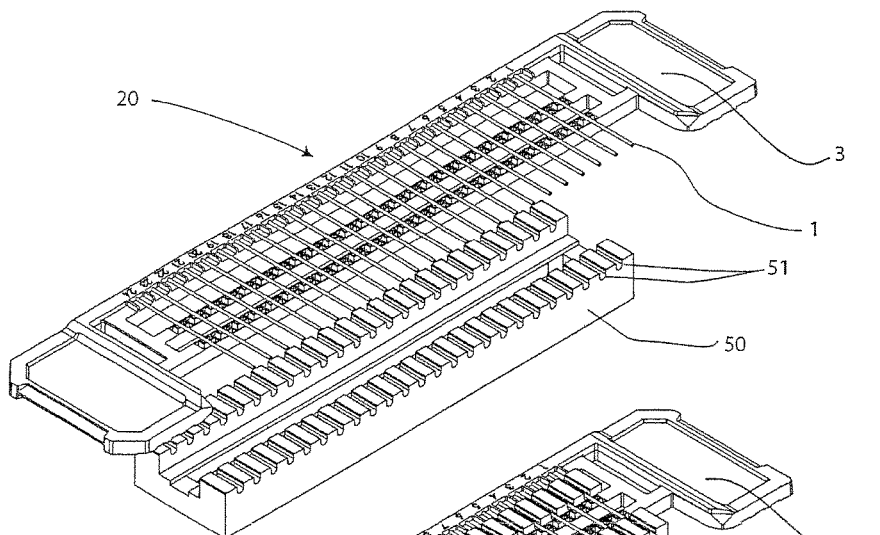
Figure 9B:
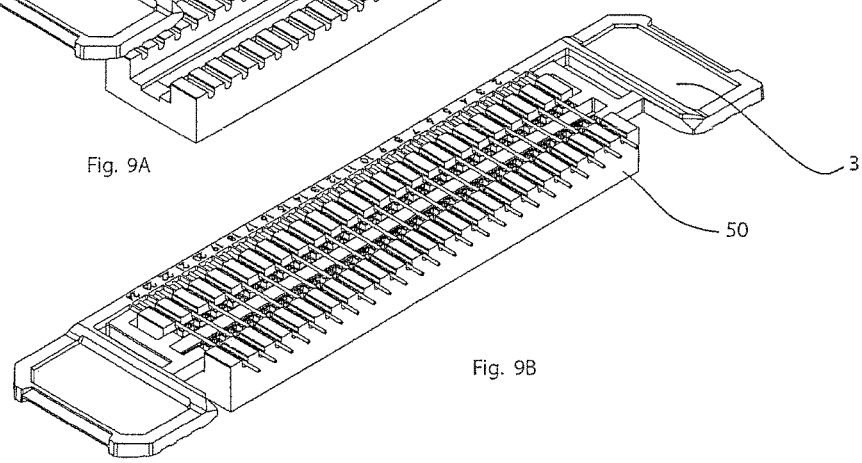
Figure 9C:
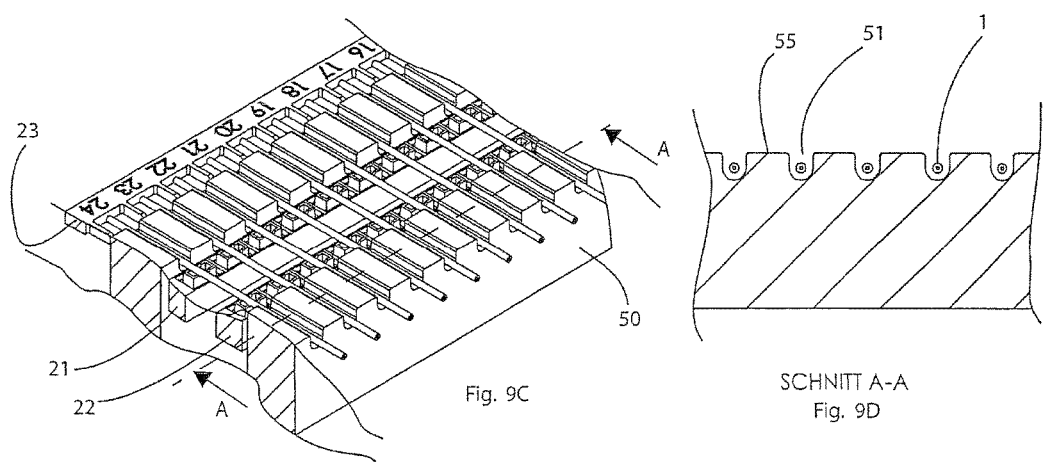
Figure 9D:
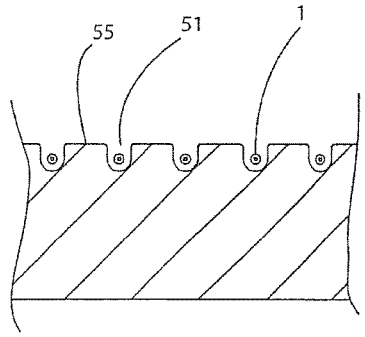

FIG. 9A exemplarily shows a tempering device for tempering the capillaries 1 of an array 20. The perspective view shows the carrier before tempering separated from the tempering device. The tempering device has a tempering body 50 having tempering partitions 55 being spaced apart from each other. Between the tempering partitions there are recesses 51 which serve for receiving the capillaries 1 (cf. FIGS. 9B, 9C and 9D). FIG. 9B shows an array 20 being positioned on the tempering body in such a way that at least one, preferably a plurality of the tempering partitions 55 lies between the capillaries. The capillaries are located in the respective recesses 51. Preferably the tempering device has at least one line of tempering partitions, preferably two lines of tempering partitions, as shown in FIGS. 9A to 9C.

The first line of tempering partitions 55 is preferably designed in such a way that they are arranged between the capillaries 1 in front of the front bridge 22 (front mounting strut) of the array 20, when the array is put into the tempering device for tempering.

It is further preferred that a second line of tempering partitions 55 is designed in such a way that it lies between the capillaries 1 and behind the middle bridge 21 (middle mounting strut), preferably between bridge 21 and the third strut 23, when the array is put into the tempering device for tempering.

In other words, the tempering partitions preferably lie in the tempering portion 6 of the array during tempering, wherein an array preferably comprises two tempering portions which preferably allow an individual or common tempering of one or more capillaries. A first tempering portion 6 of the array is preferably designed between one of the two bridges 21, 22 and the rear bridge 23 and/or between one of the two bridges 21, 22 and the free end 11.

The capillaries are preferably heated/cooled/tempered by means of a tempered air cushion between the tempering partitions and the lid (not shown). Preferably the lid is designed in such a way that it completely covers the array and the capillaries and preferably comprises an opening in the region of the measurement region 2.

A process in which a handling device is integrated may exemplarily be illustrated as follows, wherein the steps are optional: 0. Opening of the package by the grabber. 1. Removing an array from a package/stack. 2. Transporting the array to a filling position. 3. Filling the array. 4. Transporting the filled array to a tray/measurement device. 5. Depositing (and positioning) on the tray/in the measurement device. 6. After the measurement procedure: Removing the array/tray from the measurement device and transportation to a storage container (e.g. rubbish bin or intermediate storage).

Figure 11:
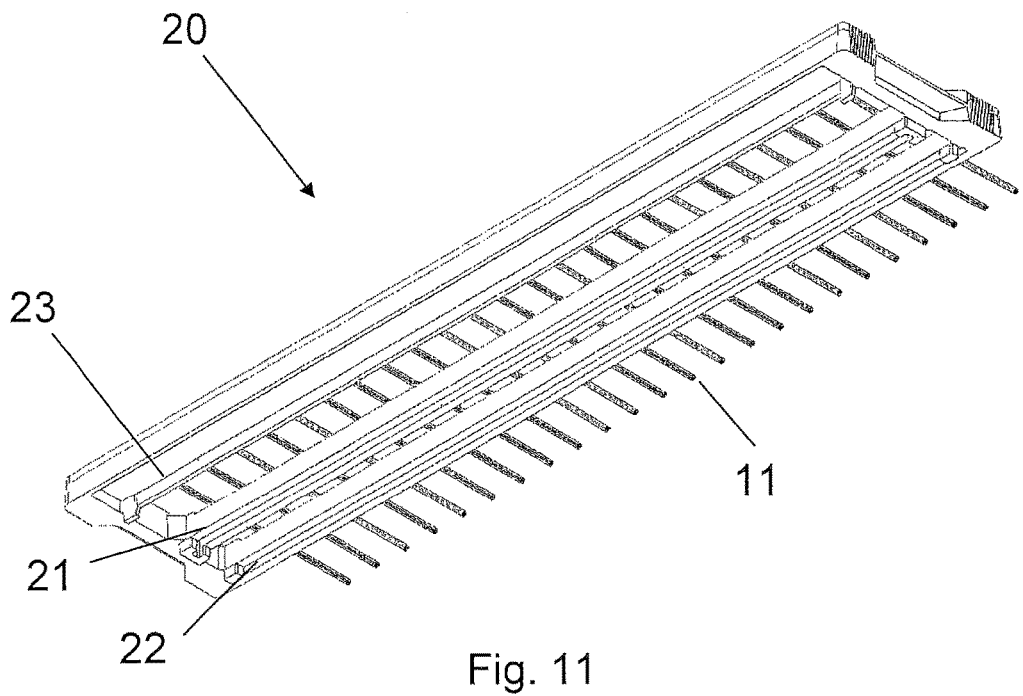
FIG. 11 a perspective view of a further alternative embodiment of the array from below.

FIG. 11 shows a perspective view of a further preferred embodiment from below. In particular, the comparison of the capillary array 20 from FIG. 6B with the alternative embodiment of FIG. 11 basically shows a very similar structure. However, in the embodiment of FIG. 11 the handle portions 3 were made smaller or left out on both sides. Said alternative embodiment is thus more compact and preferably designed for automated handling and/or space-saving.

Figure 12:
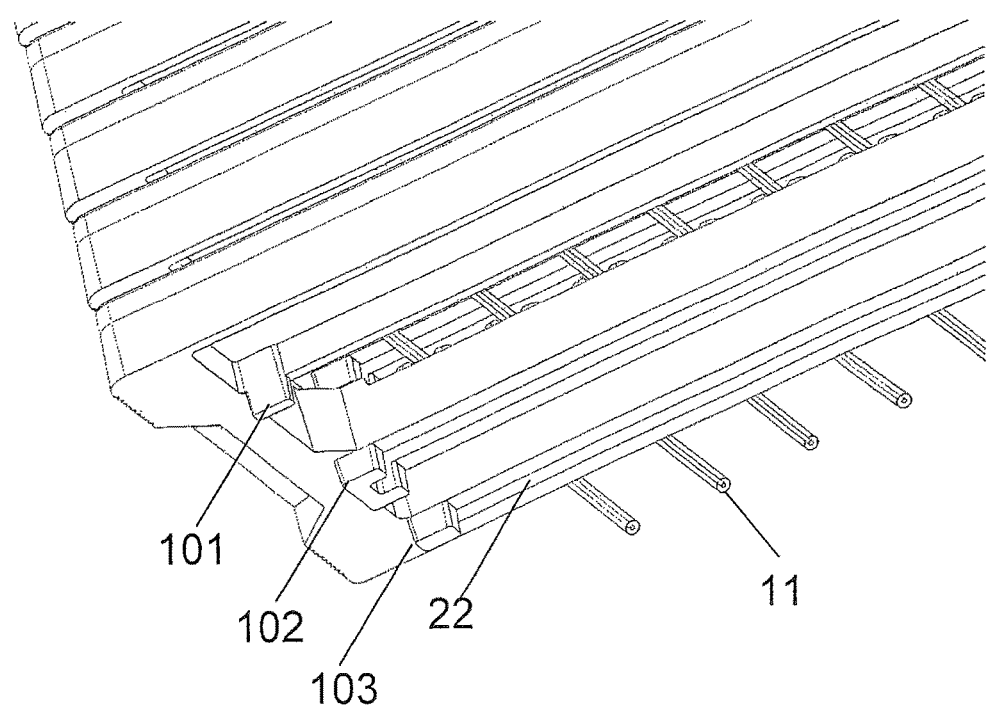
FIG. 12 a partial view of a plurality of stacked arrays according to the embodiment of FIG. 11 from below.

FIG. 12 shows a perspective detailed view of the capillary array 20 of FIG. 11. In particular, said detailed view shows teeth 101, 102, and 103 by means of which the capillary arrays 20 may easily be stacked. This is advantageous for storing, packaging as well as automated and manual handling. Preferably, the capillary arrays 20 have "teeth" 101, 102 and/or 103 which project downwards and engage with respective recesses on the upper side of the capillary array 20 lying below. The teeth and recesses are preferably designed similar to plastic building bricks for children (for example Lego®), which allow a plurality of capillary arrays 20 being easily stacked on top of each other. This has the preferred advantage that capillary arrays which are stuck together in such a way do not get out of place, i.e. the capillary arrays do not slide apart in the plane. The capillary arrays are preferably dimensioned in such a way that the capillaries of two adjacent arrays in a stack are being spaced apart 4.5 mm. In other words, the capillary arrays are so high that the capillaries of adjacent capillary arrays have a distance "b" of about 4.5 mm in height (cf. FIGS. 13 and 14), corresponding to the modular dimension of 384 multiwell plates. The distance "b" is preferably the center-to-center distance of two capillaries lying on adjacent stacked arrays and is substantially 4.5 mm. Correspondingly, for example 2 to 16 capillary arrays 20 may be stacked and simultaneously be put into a microwell plate. Preferably this also applies to for 96 (9 mm pattern→maximum of 4 capillaries per well) and 384 multiwell pates (4.5 mm pattern). When using 1536 multiwell plates (modular dimension 2.25 mm) "only" every second line is caught when having a distance b=4.5 mm; this may, however, be advantageous for certain applications. The multiwell plate may nevertheless be used completely, by immersing twice with a stack of 16.

Figure 13:
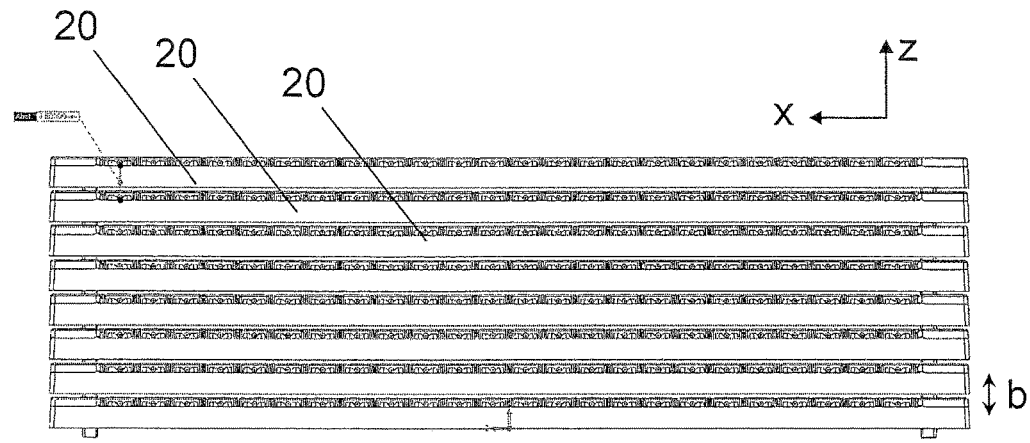
FIG. 13 a front view of eight stacked arrays according to the embodiment of FIGS. 11 and 12 with respect to the front side of the capillaries.

FIG. 13 shows a front view of eight stacked arrays 20 showing the free openings of the capillaries 11. The distance b discussed above is exemplarily drawn in for two adjacent arrays.

Furthermore, the arrangement in the 4.5×4 5 mm pattern can be seen in said view of the stacked capillary arrays 20. In other words, the capillaries are arranged in height (z-direction) as well as in "x-direction" in the 4.5 mm pattern, wherein the capillaries extend along the y-direction (cf. FIG. 14).

Figure 14:
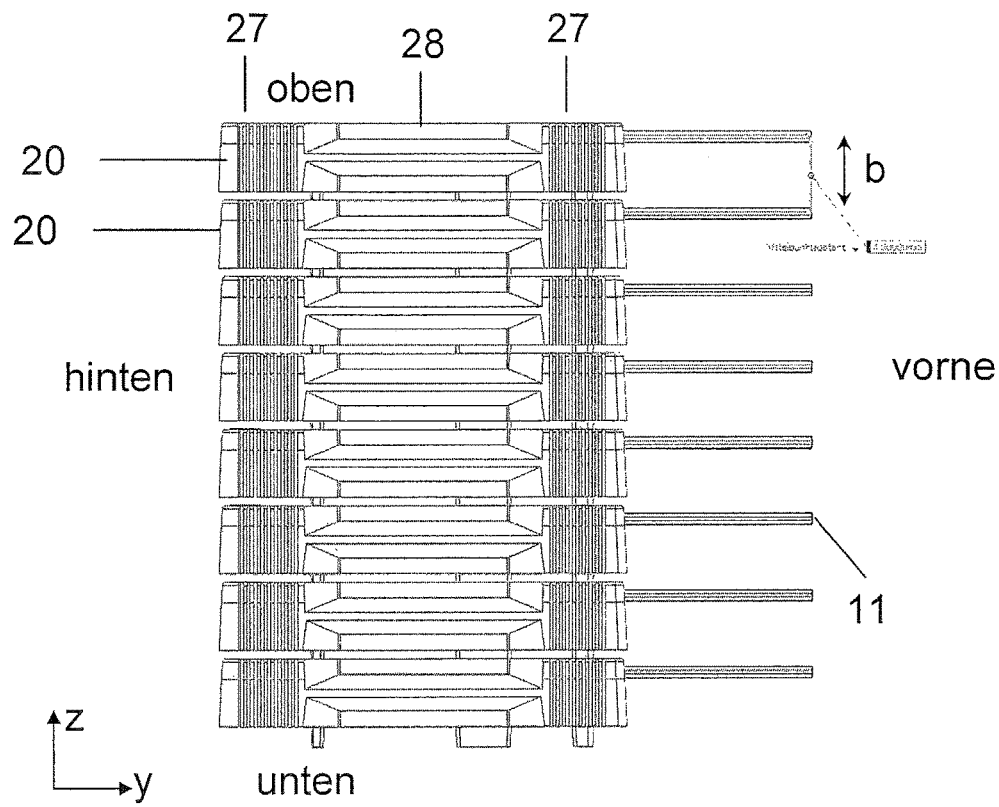
FIG. 14 a side view of the eight stacked arrays of FIG. 13.

FIG. 14 shows the stack of FIG. 13 in a side view. Again, the capillary distance of capillary chips stacked on top of each other is exemplarily shown with a distance b=4.5 mm. Furthermore, a corrugated surface 27 on the left and on the right of a "grabbing bevel" 28 is shown in said embodiment. Said two elements help the robot to grab the capillary arrays 20.

Figure 15:
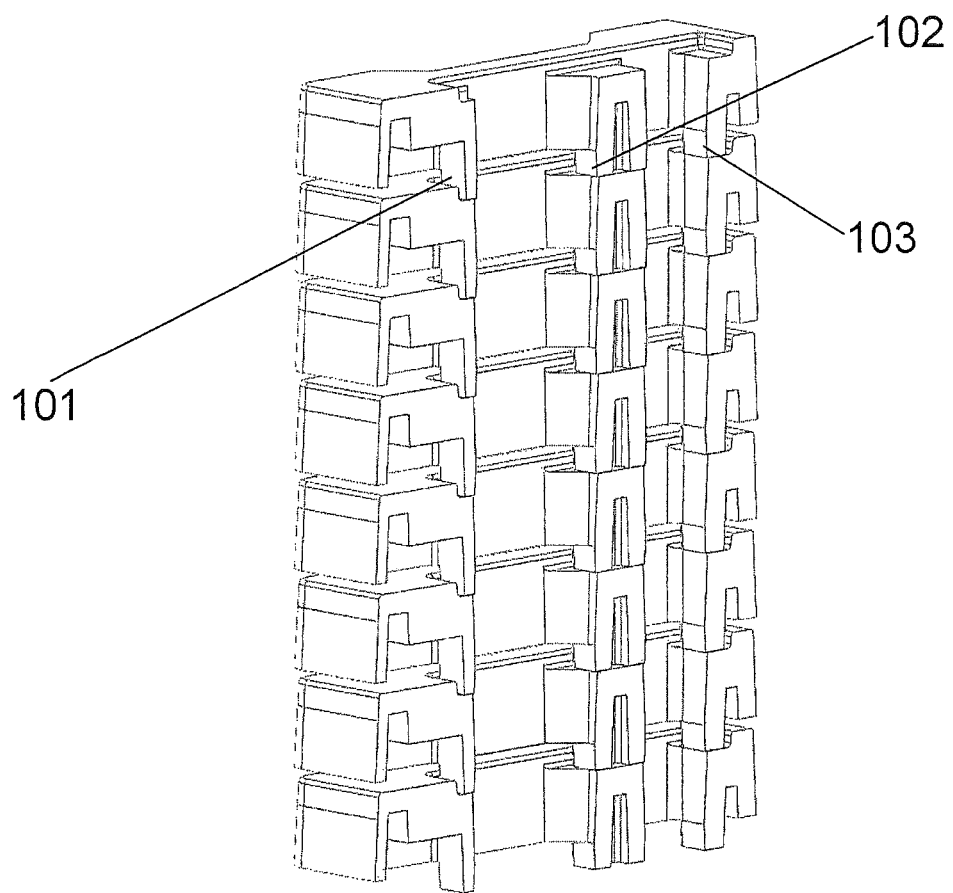
FIG. 15 a detailed view of a design of the shapes of the arrays in order to achieve a secure stackability.

FIG. 15 is a sectional view through the stacked capillary arrays 20. In said illustration it can clearly be seen how the teeth 101, 102 and 103 of the array lying above engage with respective recesses in the array 20 lying below.

The invention also comprises the accurate or exact expressions, features, numeric values or ranges etc when said expressions, features, numeric values or ranges are before or subsequently named with terms like "approximately, about, substantially, generally, at least" etc (i.e. "approximately 3 should also comprise "3" or "substantially radial" should also comprise "radial").

The invention claimed is:

1. An array comprising a plurality of glass capillaries, in particular for thermooptical measurements, wherein the capillaries are arranged in the same plane and are mechanically attached to the array, and
the array comprises at least two bridges which are substantially parallel to each other and which extend substantially transverse to the longitudinal axis of the capillaries, and are spaced apart from one another,
the capillaries are attached to the array at, at least two points or sections, wherein one point is on the first bridge and one point is on the second bridge,
the distance between adjacent capillaries amounts to approximately 2.25 mm or an integer multiple thereof,
wherein at least one first free end of each capillary projects from the array in such a way that the free ends of the capillaries are insertable simultaneously into wells of a microwell plate,
wherein the array comprises a measurement recess between both bridges so that the capillary may be screened or illuminated by means of light from a light source which radiates light substantially perpendicular to the common plane, in a central region between the first and the second end of the capillary,
wherein stacking elements in the form of one or more teeth and corresponding recesses are provided such that the tooth or the teeth engage with the corresponding recesses of another similar array, when stacked on said other array,
wherein the array comprises two tapered surfaces shaped as a wedge at opposite ends of the two bridges for an automatic handling and for automatic centering the array in a grab.

2. The array according to claim 1, wherein
i) the first free end projects 3 mm to 20 mm into a well of a microwell plate, such that only the capillaries are inserted into the well, and/or
ii) the capillaries have a length of 5 mm to 50 mm.

3. The array according to claim 1, wherein the capillaries are attached to the array in such a way that a second end of the capillaries is open in such a way that air may leak, when the first free end is filled with a liquid or is dipped into a liquid in order to be filled.

4. The array according to claim 1, wherein the array comprises a rear bridge comprising an abutment in order to cooperate with the capillaries.

5. The array according to claim 1, wherein the measurement recess has a width between 2 mm-6 mm.

6. The array according to claim 1, wherein the array comprises a tempering region which enables an individual or simultaneous tempering of one or more capillaries,
wherein the tempering region is arranged between one of the bridges and the rear bridge and/or between one of the bridges and the free end.

7. The array according to claim 1, wherein the first free end of each capillary projects from the array by projecting from one of the bridges.

8. The array according to claim 1, wherein the microwell plate is a standardized 96, 384 or 1536 microwell plate and the array comprises 4, 6, 8, 12, 16, 24, 48, or 96 capillaries.

9. The array according to claim 1, wherein the array is clearly markable, by means of at least one of the following procedures: labelling, colouring, barcode, 2D barcode, DataMatrix Code, RFID.

10. The array according to claim 1, wherein the at least one tooth projecting downwards from the lower side of the array and the at least one recess is provided on the upper side of the array for receiving the respective tooth of an array stacked on the array.

11. The array according to claim 10, wherein the distance (b) between two capillaries of two arrays stacked on top of another amounts to substantially 4.5 mm.

12. The array according to claim 1, wherein the arrays are so high that the capillaries of adjacent stacked, arrays have a distance of about 4.5 mm, in height.

13. A kit comprising at least one array according to claim 1 and a tray for receiving at least one array.

14. A method for filling a plurality of capillaries in an array, comprising
i) providing the array of claim 1, and
ii) inserting the first free ends of the capillaries simultaneously into the wells of a microwell plate thereby filling the plurality of capillaries simultaneously by means of capillary forces, or
filling a plurality of the plurality of capillaries simultaneously by means of a multichannel pipette via the first free ends.

15. The method for filling a plurality of capillaries according to claim 14, wherein the array and/or the capillaries are aligned obliquely between a horizontal and a vertical position or vertically regarding gravitation.

16. The method according to claim 14, wherein the method further comprises at least one of the following, steps conducted in an automated way:
   1. removing an array from a package/stack
   2. transporting the array to a filling position
   3. filling the array
   4. transporting the filled array to a tray/measurement device
   5. positioning on the tray/in the measurement device
   6. conducting a measuring procedure
   7. removing the array/tray from the measurement device and transportation to a storage container (e.g. rubbish bin or intermediate storage).

17. A system comprising
the array of claim 1,
a filling station for filling the capillaries of the array, wherein the filling station comprises a mounting for the array and the array is preferably tilted at an angle between 0° to 180° to gravitational force.

18. A system comprising
the array of claim 1,
a tempering device for tempering the capillaries of the array, wherein the tempering device comprises a tempering body with tempering partitions being spaced apart from each other, and the array may be laid onto the tempering body in such a way that at least one, preferably a plurality of the tempering partitions lie between the capillaries.

\* \* \* \* \*